United States Patent [19]

Nasu et al.

[11] Patent Number: 4,995,898
[45] Date of Patent: Feb. 26, 1991

[54] IMIDAZOLE COMPOUNDS AND BIOCIDAL COMPOSITION COMPRISING THE SAME FOR CONTROLLING HARMFUL ORGANISMS

[75] Inventors: Rikuo Nasu; Terumasa Komyoji; Toshio Nakajima; Kazumi Suzuki; Keiichiro Ito; Takeshi Oshima; Hideshi Yoshimura, all of Shiga, Japan

[73] Assignee: Ishihara Sangyo Kaisha, Ltd., Osaka, Japan

[21] Appl. No.: 168,070

[22] Filed: Mar. 14, 1988

[30] Foreign Application Priority Data

Mar. 13, 1987 [JP] Japan .................................. 62-58451
Apr. 3, 1987 [JP] Japan .................................. 62-82546
Apr. 30, 1987 [JP] Japan ................................ 62-106577

[51] Int. Cl.$^5$ .................... A01N 43/26; C07D 233/90
[52] U.S. Cl. ............................................. 71/90; 71/92; 544/58.4; 544/58.5; 544/139; 546/210; 546/278; 548/110; 548/336; 548/337; 548/339; 514/227.8; 514/235.8; 514/326; 514/34; 514/398; 514/397
[58] Field of Search ............... 548/110, 336, 337, 339; 546/210, 278; 544/139, 58.4, 58.5; 514/227.8, 235.8, 326, 341, 397, 398; 71/90, 92

[56] References Cited

U.S. PATENT DOCUMENTS

| | | | |
|---|---|---|---|
| 3,609,157 | 9/1971 | Allan et al. | 260/295 |
| 3,681,369 | 8/1972 | Doherty | 260/296 H |
| 4,220,466 | 9/1980 | Patel | 71/92 |
| 4,536,502 | 8/1985 | Giravdon | 514/234.5 |
| 4,574,010 | 3/1986 | Leone-Bay et al. | 71/92 |
| 4,579,853 | 4/1986 | Giravdon et al. | 514/303 |
| 4,659,720 | 4/1987 | Chabala | 548/337 X |

FOREIGN PATENT DOCUMENTS

| | | |
|---|---|---|
| 830719 | 12/1975 | Belgium . |
| 845641 | 2/1977 | Belgium . |
| 852313 | 9/1977 | Belgium . |
| 0031086 | 7/1981 | European Pat. Off. . |
| 219192 | 4/1987 | European Pat. Off. . |
| 239508 | 9/1987 | European Pat. Off. . |
| 0284277 | 9/1988 | European Pat. Off. . |
| 1770850 | 1/1972 | Fed. Rep. of Germany . |
| 2317453 | 10/1973 | Fed. Rep. of Germany . |
| 2634053 | 2/1978 | Fed. Rep. of Germany . |
| 2559150 | 8/1985 | France . |
| 5004303 | 1/1980 | Japan . |
| 62072 | 5/1980 | Japan . |
| 15625 | 4/1985 | Japan . |
| 308523 | 9/1985 | Japan . |
| 103873 | 5/1986 | Japan . |
| 137782 | 6/1986 | Japan . |
| 175274 | 7/1986 | Japan . |
| 22782 | 1/1987 | Japan . |
| 142164 | 6/1987 | Japan . |
| 195379 | 8/1987 | Japan . |

OTHER PUBLICATIONS

Recl. Trav. Chim. Pyas–Bas, 1973, 92(3), 449–459.
J. Org. Chem., vol. 44, No. 16, 1979, 2902–2906.
J. Org. Chem., vol. 51, No. 10, 1986, 1891–1894.
Research Disclosure, Jun. (1986), 323–324.
Chemical Abstracts, 95: 7283q.
Chemical Abstracts, 101:7092u.
Chemical Abstracts, 106: 1383248x (1987).
Chemical Abstracts, vol. 92, No. 21, May 26, 1980, p. 656, col. 2, Abstract No. 181177f.
Chemical Abstracts, vol. 105, No. 3, Jul. 21, 1986, p. 288, col. 2, Abstract No. 20528t.
Chemical Abstracts, vol. 107, No. 19, Nov. 9, 1987, p. 726, col. 2, Abstract No. 176038k.

Primary Examiner—Richard L. Raymond
Attorney, Agent, or Firm—Sughrue, Mion, Zinn, Macpeak & Seas

[57] ABSTRACT

Novel imidazole compounds are disclosed, which are represented by the following general formula:

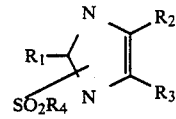

wherein:

$R_1$ represents a cyano group or a —CSNHR$_5$ group, wherein R$_5$ represents a hydrogen atom, a C$_{1-4}$ alkyl group, or a —COR$_6$ group, wherein R$_6$ represents a C$_{1-4}$ alkyl group, a halogenated C$_{1-4}$ alkyl group, or a phenyl group;

$R_2$ and $R_3$ each represents a hydrogen atom; a halogen atom; a nitro group; a cyano group; a trimethylsilyl group; a C$_{3-6}$ cycloalkyl group; a naphthyl group; a C$_{1-12}$ alkyl group which is optionally substituted with one or more halogen atoms, hydroxyl groups, acetoxy groups, C$_{1-4}$ alkoxy groups, halogenated C$_{1-4}$ alkoxy groups, phenyl groups, halogenated phenyl groups, or C$_{1-4}$ alkylated phenyl groups; a C$_{2-10}$ alkenyl group which is optionally substituted with one or more halogen atoms; a C$_{1-6}$ alkoxy group which is optionally substituted with one or more halogen atoms; a phenyl group which is optionally substituted with one or more halogen atoms, C$_{1-4}$ alkyl groups, halogenated C$_{1-4}$ alkyl groups, C$_{1-4}$ alkoxy groups, halogenated C$_{1-4}$ alkoxy groups, C$_{1-4}$ alkylthio groups, halogenated C$_{1-4}$ alkylthio groups, nitro groups, cyano groups, or 3,4-methylenedioxy groups; a furyl group which is optionally substituted with one or more halogen atoms or C$_{1-4}$ alkyl groups; a thienyl group which is optionally substituted with one or more halogen atoms or C$_{1-4}$ alkyl groups; a pyridyl group which is optionally substituted with one or more halogen atoms or C$_{1-4}$ alkyl groups; an —SO$_n$R$_7$ group, wherein R$_7$ represents a C$_{1-6}$ alkyl group, a C$_{2-6}$ alkenyl group, a phenyl group which is optionally substituted with one or more halogen (Abstract continued on next page.)

atoms, a benzyl group, a pyridyl group which is optionally substituted with one or more halogen atoms, $C_{1-4}$ alkyl groups, or halogenated $C_{1-4}$ alkyl groups; or an $-NR_8R_9$ group, wherein $R_8$ and $R_9$ each represents a $C_{1-4}$ alkyl group, and n is 0, 1, or 2; or a $-CO(NH)_mR_{10}$ group, wherein $R_{10}$ represents a $C_{1-4}$ alkyl group which is optionally substituted with one or more halogen atoms, a $C_{1-4}$ alkoxy group which is optionally substituted with one or more halogen atoms, or a phenyl group which is optionally substituted with one or more halogen atoms; and m is 0 or 1; and $R_4$ represents a $C_{1-6}$ alkyl group which is optionally substituted with one or more halogen atoms; a $C_{3-6}$ cycloalkyl group; a phenyl group; a thienyl group; or an $-NR_{11}R_{12}$ group, wherein $R_{11}$ and $R_{12}$ each represents a hydrogen atom, a $C_{1-4}$ alkyl group which is optionally substituted with one or more halogen atoms, a $C_{2-4}$ alkenyl group, or $R_{11}$ and $R_{12}$ are combined with each other together with a nitrogen atoms adjacent thereto to form a pyrrolidinyl group, a piperidinyl group, a morpholino group, or a thiomorpholino group, provided that $R_{11}$ and $R_{12}$ are not simultaneously a hydrogen atom;

provided that $R_2$ and $R_3$ are not simultaneously a halogen atom. The compounds are effective as biocides.

9 Claims, No Drawings

IMIDAZOLE COMPOUNDS AND BIOCIDAL COMPOSITION COMPRISING THE SAME FOR CONTROLLING HARMFUL ORGANISMS

FIELD OF THE INVENTION

The present invention relates to novel imidazole compounds and biocidal compositions comprising the same for controlling harmful organisms.

BACKGROUND OF THE INVENTION

Imidazole type compounds proposed so far are exemplified below.

Belgian Patent No. 852313 (published Sept. 12, 1977) discloses (4,5)-dichloro-imidazole(2)-carboxylic acid derivatives having the formula

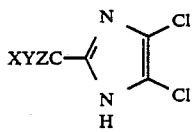

wherein CXYZ represents a C atom with 3 bonds attached to hetero atoms, and Japanese Patent Publication No. 15625/85 (published Apr. 20, 1985) discloses the following reaction scheme,

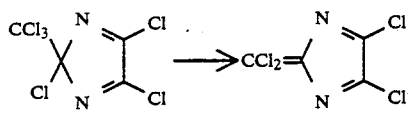

while no compound having other substituents than chlorine atoms at the 4 and 5-positions in the imidazole ring and having a substituted sulfonyl group in the imidazole ring is disclosed in both of the above references.

Recl. Trav. Chim. Pays-Bas, 1973, 92(3), 449-59 discloses

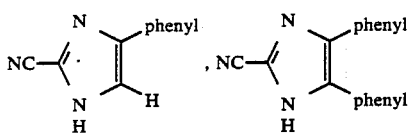

etc.;

DT-OS No. 2317453 (published Oct. 11, 1973) discloses quaternary ammonium salts of

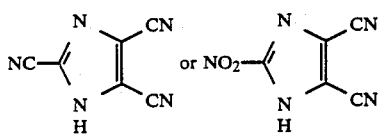

etc.; J. Org. Chem., Vol. 44, No. 16, 1979, 2902-2906 discloses

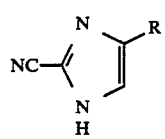

(R: H, $CH_3$), etc.; EP No. 31086 (published July 1, 1981) discloses

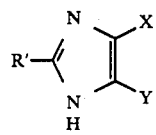

(R': $-CQZR$, CN) J. Org. Chem., Vol. 51, No. 10, 1986, 1891-1894 discloses 2-cyano imidazole, etc.; and Research Disclosure, June (1986), 323-324 (C.A., 106, 49942e) discloses

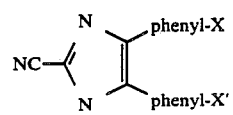

etc.; while no compound having a substituted sulfonyl group in the imidazole ring is disclosed in any of the above-described references.

Japanese Patent Application (OPI) No. 4303/80 (published Jan. 12, 1980) (the term "OPI" as used herein means a "published unexamined patent application") discloses 1-(N,N-dimethylsulfamoyl)-4,5-dicyanoimidazole

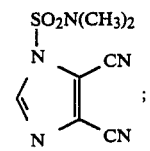

C.A., 95: 7283q [Japanese Patent Application (OPI) No. 157570/80 (published Dec. 8, 1980)] discloses sulfamoylimidazole derivatives of

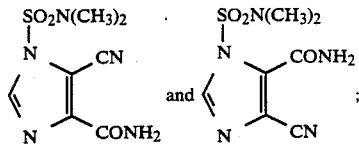

C.A., 101: 7092u (J. Chem. Soc., Perkin Trans. 1, 1984, (3), 481-6) discloses

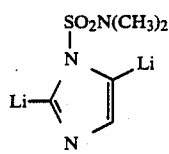

etc.; and C.A., 106: 138324x (Tetrahedron, 1986, 42(8), 2351-8) discloses

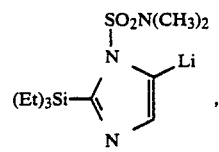

etc.; while no compounds having other than a hydrogen atom, a lithium atom, or an —Si(Et)$_3$ group at the 2-position in the imidazole ring as a substituent are disclosed.

Japanese Patent Application (OPI) No. 142164/87 (published June 25, 1987) discloses 4,5-dichloroimidazole compounds having the formula

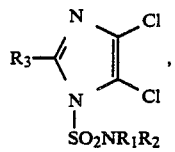

while no compounds having other substituents than chlorine atoms at the 4 and 5-positions in the imidazole ring are disclosed.

References listed below disclose imidazopyridine compounds and/or benzimidazole compounds in which the compounds contain a condensed ring of an imidazole ring with a benzene ring and/or a pyridine ring in their chemical structures.

U.S. Pat. No. 3,609,157 (issued Sept. 28, 1971)
U.S. Pat. No. 3,681,369 (issued Aug. 1, 1972)
Belgian Patent No. 830719 (published Dec. 29, 1975)
Belgian Patent No. 845641 (published Feb. 28, 1977)
U.S. Pat. No. 4,536,502 (issued Aug. 20, 1985)
U.S. Pat. No. 4,579,853 (issued Apr. 1, 1986)
French Patent No. 2559150 (published Aug. 9, 1985)
Japanese Patent Application (OPI) No. 103873/86 (published May 22, 1086)
Japanese Patent Application (OPI) No. 22782/87 (published Jan. 30, 1987)
EP No. 219192 (published Apr. 22, 1987)
Japanese Patent Application (OPI) No. 195379/87 (published Aug. 28, 1987)
EP No. 239508 (published Sept. 30, 1987)

SUMMARY OF THE INVENTION

An object of the present invention is to provide imidazole compounds of the following general formula (I) and biocidal compositions comprising the same for controlling harmful organisms:

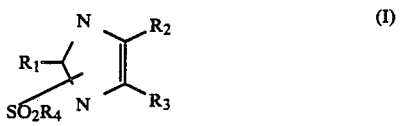

wherein $R_1$ represents a cyano group or a —CSNHR$_5$ group, wherein $R_5$ represents a hydrogen atom, a $C_{1-4}$ alkyl group, or a —COR$_6$ group, wherein $R_6$ represents a $C_{1-4}$ alkyl group, a halogenated $C_{1-4}$ alkyl group, or a phenyl group;

$R_2$ and $R_3$ each represents a hydrogen atom; a halogen atom; a nitro group; a cyano group; a trimethylsilyl group; a $C_{3-6}$ cycloalkyl group; a naphthyl group; a $C_{1-12}$ alkyl group which is optionally substituted with one or more halogen atoms, hydroxyl groups, acetoxy groups, $C_{1-4}$ alkoxy groups, halogenated $C_{1-4}$ alkoxy groups, phenyl groups, halogenated phenyl groups, or $C_{1-4}$ alkylated phenyl groups; a $C_{2-10}$ alkenyl group which is optionally substituted with one or more halogen atoms; a $C_{1-6}$ alkoxy group which is optionally substituted with one or more halogen atoms; a phenyl group which is optionally substituted with one or more halogen atoms, $C_{1-4}$ alkyl groups, halogenated $C_{1-4}$ alkyl groups, $C_{1-4}$ alkoxy groups, halogenated $C_{1-4}$ alkoxy groups, $C_{1-4}$ alkylthio groups, halogenated $C_{1-4}$ alkylthio groups, nitro groups, cyano groups, or 3,4-methylenedioxy groups; a furyl group which is optionally substituted with one or more halogen atoms or $C_{1-4}$ alkyl groups; a thienyl group which is optionally substituted with one or more halogen atoms or $C_{1-4}$ alkyl groups; a pyridyl group which is optionally substituted with one or more halogen atoms or $C_{1-4}$ alkyl groups; an —SO$_n$R$_7$ group, wherein $R_7$ represents a $C_{1-6}$ alkyl group, a $C_{2-6}$ alkenyl group, a phenyl group which is optionally substituted with one or more halogen atoms, a benzyl group, a pyridyl group which is optionally substituted with one or more halogen atoms, $C_{1-4}$ alkyl groups, or halogenated $C_{1-4}$ alkyl groups; or an —NR$_8$R$_9$ group, wherein $R_8$ and $R_9$ each represents a $C_{1-4}$ alkyl group, and n is 0, 1, or 2; or a —CO(NH)$_m$R$_{10}$ group, wherein $R_{10}$ represents a $C_{1-4}$ alkyl group which is optionally substituted with one or more halogen atoms, a $C_{1-4}$ alkoxy group which is optionally substituted with one or more halogen atoms, or a phenyl group which is optionally substituted with one or more halogen atoms; and m is 0 or 1; and $R_4$ represents a $C_{1-6}$ alkyl group which is optionally substituted with one or more halogen atoms; a $C_{3-6}$ cycloalkyl group; a phenyl group; a thienyl group; or an —NR$_{11}$R$_{12}$ group, wherein $R_{11}$ and $R_{12}$ each represents a hydrogen atom, a $C_{1-4}$ alkyl group which is optionally substituted with one or more halogen atoms, a $C_{2-4}$ alkenyl group, or $R_{11}$ and $R_{12}$ are combined with each other together with a nitrogen atom adjacent thereto to form a pyrrolidinyl group, a piperidinyl group, a morpholino group, or a thiomorpholino group, provided that $R_{11}$ and $R_{12}$ are not simultaneously a hydrogen atom;

provided that $R_2$ and $R_3$ are not simultaneously a halogen atom.

Another object of the present invention is to provide a process for preparing the imidazole compounds of the formula (I) hereinabove.

A further object of the present invention is to provide intermediate compounds of the following general formula (II'):

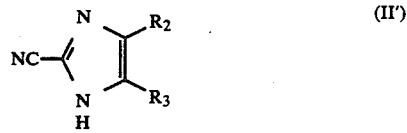

wherein $R_2$ and $R_3$ each represents a hydrogen atom; a halogen atom; a nitro group; a cyano group; a trimethylsilyl group; a $C_{3-6}$ cycloalkyl group; a naphthyl group; a $C_{1-12}$ alkyl group which is optionally substituted with one or more halogen atoms, hydroxyl groups, acetoxy groups, $C_{1-4}$ alkoxy groups, halogenated $C_{1-4}$ alkoxy groups, phenyl groups, halogenated phenyl groups, or $C_{1-4}$ alkylated phenyl groups; a $C_{2-10}$ alkenyl group which is optionally substituted with one or more halogen atoms; a $C_{1-6}$ alkoxy group which is optionally substituted with one or more halogen atoms; a phenyl group which is optionally substituted with one or more halogen atoms, $C_{1-4}$ alkyl groups, halogenated $C_{1-4}$ alkyl groups, $C_{1-4}$ alkoxy groups halogenated $C_{1-4}$ alkoxy groups, $C_{1-4}$ alkylthio groups, halogenated $C_{1-4}$ alkylthio groups, nitro groups, cyano groups, or 3,4-methylenedioxy groups; a furyl group which is optionally substituted with one or more halogen atoms or $C_{1-4}$ alkyl groups; a thienyl group which is optionally substituted with one or more halogen atoms or $C_{1-4}$ alkyl groups; a pyridyl group which is optionally substituted with one or more halogen atoms or $C_{1-4}$ alkyl groups; an $-SO_nR_7$ group, wherein $R_7$ represents a $C_{1-6}$ alkyl group, a $C_{2-6}$ alkenyl group, a phenyl group which is optionally substituted with one or more halogen atoms, a benzyl group, a pyridyl group which is optionally substituted with one or more halogen atoms, $C_{1-4}$ alkyl groups, or halogenated $C_{1-4}$ alkyl groups; or an $-NR_8R_9$ group, wherein $R_8$ and $R_9$ each represents a $C_{1-4}$ alkyl group, and n is 0, 1, or 2; or a $-CO(NH)_m$ $R_{10}$ group, wherein $R_{10}$ represents a $C_{1-4}$ alkyl group which is optionally substituted with one or more halogen atoms, a $C_{1-4}$ alkoxy group which is optionally substituted with one or more halogen atoms, or a phenyl group which is optionally substituted with one or more halogen atoms; and m is 0 or 1, provided that compounds represented by the following general formula (II''):

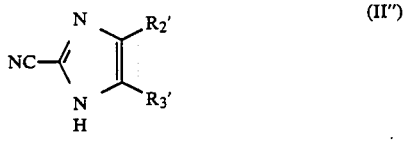

wherein $R_2'$ and $R_3'$ are simultaneously a hydrogen atom, a halogen atom, a cyano group, or a phenyl group which is optionally substituted with same or different $C_{1-2}$ alkoxy group or $C_{1-2}$ alkylthio group at the para-position; and wherein $R_2'$ is a hydrogen atom and $R_3'$ is a methyl group or a phenyl group, are excluded.

Among the imidazole compounds represented by the general formula (I), preferred compounds of the present invention are illustrated below.

Compounds of the general formula (I) wherein $R_1$ is a cyano group;

Compounds of the general formula (I) wherein $R_2$ and $R_3$ each represents a hydrogen atom; a halogen atom; a nitro group; a cyano group; a $C_{1-12}$ alkyl group which is optionally substituted with one or more halogen atoms, hydroxyl groups, $C_{1-4}$ alkoxy groups, phenyl groups, halogenated phenyl groups, or $C_{1-4}$ alkylated phenyl groups; a $C_{2-10}$ alkenyl group which is optionally substituted with one or more halogen atoms; a phenyl group which is optionally substituted with one or more halogen atoms, $C_{1-4}$ alkyl groups, $C_{1-4}$ alkoxy groups, halogenated $C_{1-4}$ alkoxy groups or nitro groups; an $-SO_nR_7$ group, wherein $R_7$ represents a $C_{1-6}$ alkyl group, a phenyl group which is optionally substituted with one or more halogen atoms; or an $-NR_8R_9$ group, wherein $R_8$ and $R_9$ each represents a $C_{1-4}$ alkyl group, and n is 0, 1, or 2; or a $-CONHR_{10}$ group, wherein $R_{10}$ represents a phenyl group which is optionally substituted with one or more halogen atoms, provided that $R_2$ and $R_3$ are not simultaneously a halogen atom;

Compounds of the general formula (I) wherein $R_4$ is a $C_{1-6}$ alkyl group or an $-NR_{11}R_{12}$ group, wherein $R_{11}$ and $R_{12}$ each represents a $C_{1-4}$ alkyl group;

Compounds of the general formula (I) wherein $R_2$ is a hydrogen atom; a $C_{1-12}$ alkyl group which is optionally substituted with one or more halogen atoms, phenyl groups, or halogenated phenyl groups; a $C_{2-4}$ alkenyl group; a phenyl group which is optionally substituted with one or more halogen atoms, $C_{1-4}$ alkyl groups, $C_{1-4}$ alkoxy groups or halogenated $C_{1-4}$ alkoxy groups; a $C_{1-6}$ alkylthio group; or a phenylthio group which is optionally substituted with one or more halogen atoms;

Compounds of the general formula (I) wherein $R_3$ is a hydrogen atom, a halogen atom, or a cyano group;

Compounds of the general formula (I) wherein $R_4$ is an $-N(CH_3)_2$ group;

Compounds of the general formula (I) wherein $R_2$ is a $C_{1-12}$ alkyl group which is optionally substituted with one or more halogen atoms, phenyl groups, or halogenated phenyl groups; a $C_{2-4}$ alkenyl group; a phenyl group which is optionally substituted with one or more halogen atoms; or a $C_{1-6}$ alkylthio group;

Compounds of the general formula (I) wherein $R_3$ is a halogen atom; and

Compounds of the general formula (I) wherein $R_1$ represents a cyano group; $R_2$ represents a $C_{1-12}$ alkyl group or a phenyl group; $R_3$ represents a chlorine atom; and $R_4$ represents an $-N(CH_3)_2$ group.

DETAILED DESCRIPTION OF THE INVENTION

In the general formula (I) described above, definitions of $C_{1-4}$ alkyl group and alkyl moieties of $C_{1-4}$ alkoxy group and $C_{1-4}$ alkylthio group may include methyl, ethyl, n-propyl, isopropyl, n-butyl, sec-butyl, isobutyl and tert-butyl groups. Definition of $C_{1-6}$ alkyl group may include n-pentyl and n-hexyl groups in addition to the exemplified $C_{1-4}$ alkyl groups hereinabove. Definition of $C_{1-12}$ alkyl group may include heptyl, octyl, nonyl, and decyl groups in addition to the exemplified $C_{1-6}$ alkyl groups hereinabove. Definition of $C_{3-6}$ cycloalkyl group may include cyclopropyl, cyclobutyl, cyclopentyl, and cyclohexyl groups. Definition of $C_{2-4}$ alkenyl group may include an allyl group, etc. Definition of $C_{2-6}$ alkenyl group may include a pentenyl group, etc. in addition to the exemplified $C_{2-4}$ alkenyl groups hereinabove. Definition of $C_{2-10}$ alkenyl group may include a geranyl group, etc. in addition to the exemplified $C_{2-6}$ alkenyl groups hereinabove. Definition of halogen atom may include chlorine, bromine, fluorine, and iodine atoms.

The novel imidazole compound represented by the general formula (I) described above can be prepared specifically by the following process:

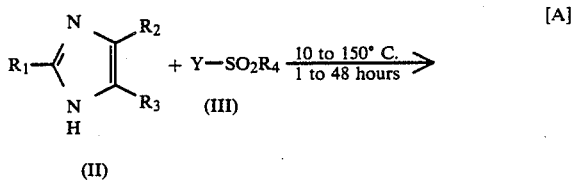

wherein $R_1$, $R_2$, $R_3$, and $R_4$ have the same meanings as described above; and Y is a halogen atom.

In the general formula (I) described above, compounds wherein $R_1$ is a cyano group can also be prepared by the following process;

[B]

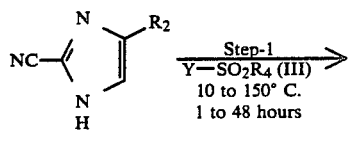
(II-1)

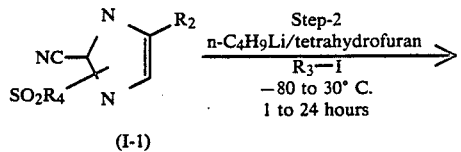
(I-1)

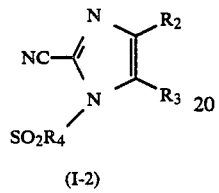
(I-2)

In the general formula (I-2) described above wherein $R_3$ is an —$SR_7$ group, $R_7SSR_7$ can also be used instead of $R_3$—I in Step-2 of the process [B] described above. In the foregoing formulae, $R_2$, $R_3$, $R_4$, $R_7$, and Y have the same meanings as described above.

In the general formula (I) described above, compounds wherein $R_1$ is a cyano group, and $R_3$ is a hydrogen atom, a chlorine atom, or a bromine atom can also be prepared by the following process:

[C]

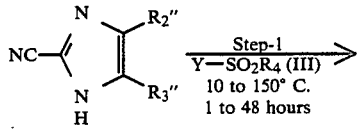
(II-2)

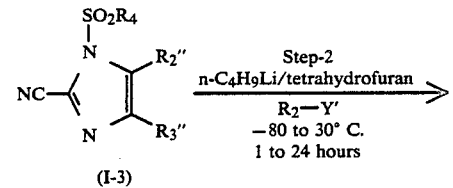
(I-3)

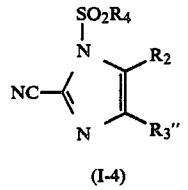
(I-4)

In the general formula (I-4) described above wherein $R_2$ is an —$SR_7$ group, $R_7SSR_7$ can also be used instead of $R_2$—Y' in Step-2 of the process [C] described above; and wherein $R_2$ is a —CH(OH)—$R_{13}$ group (wherein $R_{13}$ is an alkyl group or an optionally substituted phenyl group), $R_{13}$—CHO can also be used instead of $R_2$—Y' in Step-2 of the process [C] described above. In the foregoing formulae, $R_2$, $R_4$, and $R_7$ have the same meanings as described above; $R_2''$ and $R_3''$ are simultaneously a hydrogen atom, a chlorine atom or a bromine atom;

and Y' is a chlorine atom, a bromine atom, or a iodine atom.

In the general formula (I) described above, compounds wherein $R_1$ is a —$CSNH_2$ group or a —CSNH-$COR_6$ group can also be prepared by the following process:

[D]

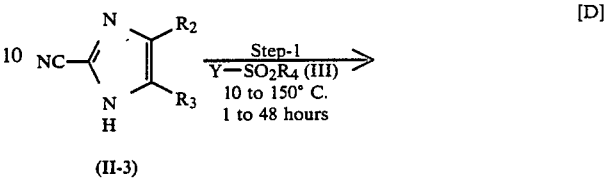
(II-3)

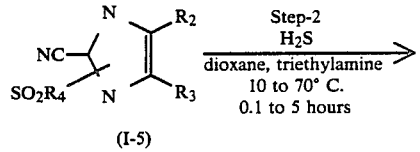
(I-5)

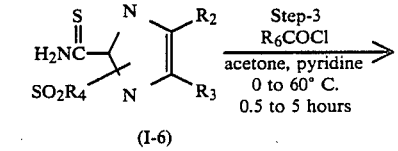
(I-6)

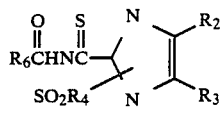
(I-7)

wherein $R_2$, $R_3$, $R_4$, $R_6$, and Y have the same meanings as described above.

The process [A] and Step-1 of the processes [B] through [D] described above are carried out, if necessary and desired, in the presence of a solvent and an acid acceptor.

Examples of the solvent include aromatic hydrocarbons such as benzene, toluene, xylene, chlorobenzene, etc.; cyclic or acyclic aliphatic hydrocarbons such as chloroform, carbon tetrachloride, methylene chloride, dichloroethane, trichloroethane, n-hexane, cyclohexane, etc.; ethers such as diethyl ether, dioxane, tetrahydrofuran, etc.; ketones such as acetone, methyl ethyl ketone, methyl isobutyl ketone, etc.; nitriles such as acetonitrile, propionitrile, etc.; and aprotic polar solvents such as dimethylformamide, N-methylpyrrolidone, dimethyl sulfoxide, sulfolane, etc.

As the acid acceptor, any of inorganic bases and organic bases can be used. Examples of the inorganic base include alkali metal hydroxides such as sodium hydroxide, potassium hydroxide, etc.; alkali metal or alkaline earth metal carbonates such as anhydrous potassium carbonate, anhydrous calcium carbonate, etc.; alkali metal hydrides such as sodium hydride; alkali metals such as metallic sodium; etc. Further, as the organic base, metion may be made of triethylamine, etc.

The reaction described above can be carried out in the presence of a suitable catalyst. As the catalyst, mention may be made of, for example, a phase transfer catalyst such as a quaternary ammonium derivative.

As the halongen atom shown by Y in the general formula (III) described above, mention may be made of a chlorine atom, a bromine atom, an iodine atom, and a fluorine atom; of these, preferred is a chlorine atom.
In the reaction scheme described above, the compounds represented by the general formula (III) are known compounds, and the compounds represented by the general formula (II) can be prepared by either one of the following processes.
(1)
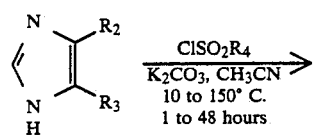
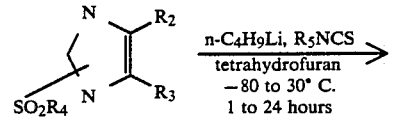
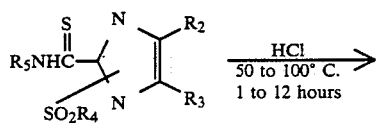
(2)
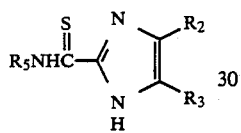
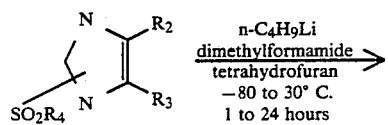
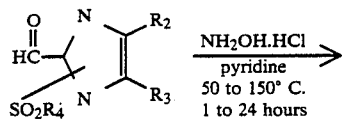
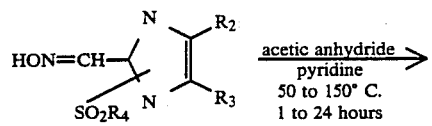
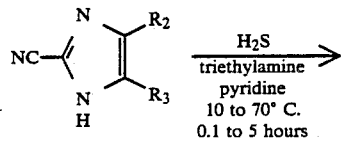
(3)
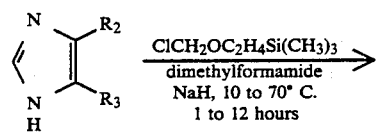
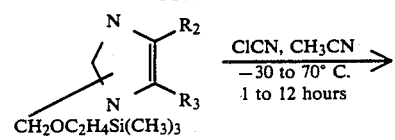
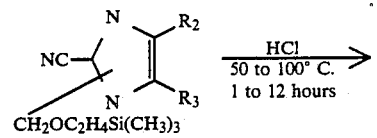
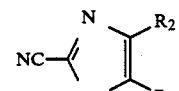
(4)
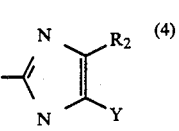
(5)
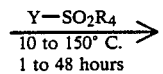
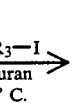
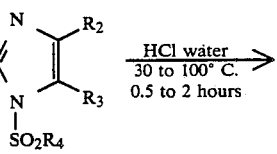
(6)
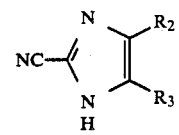
(7)
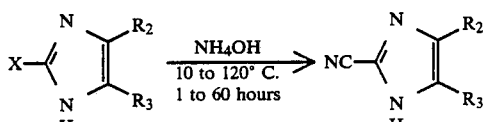
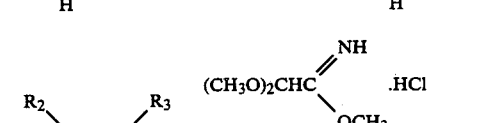
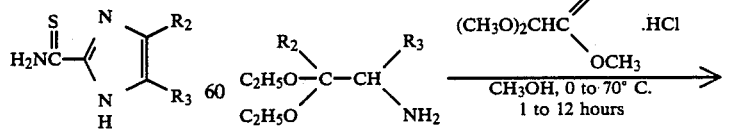
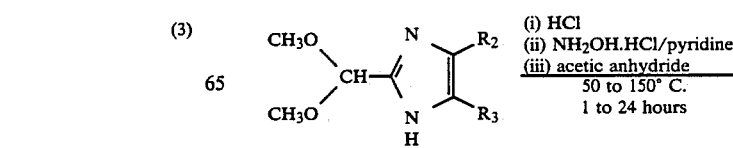

-continued
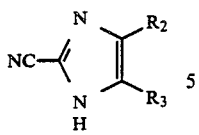
5
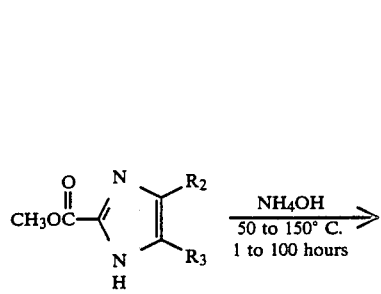
(8)
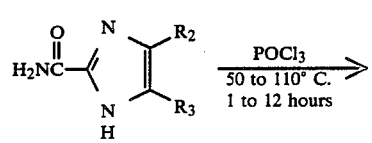
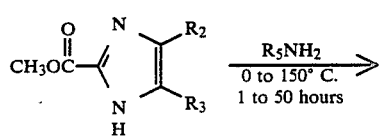
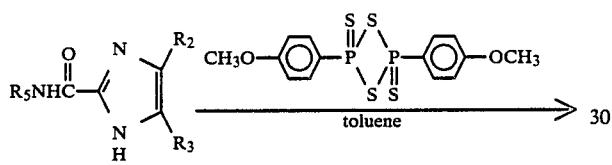
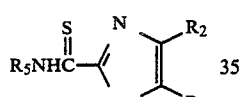
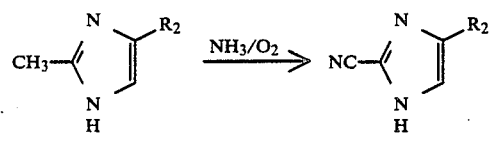
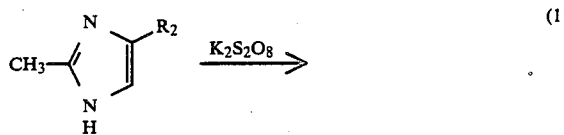
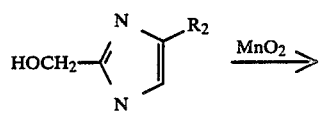
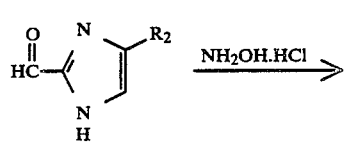
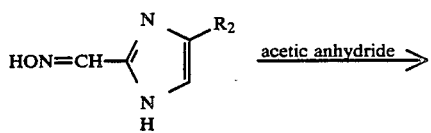
-continued
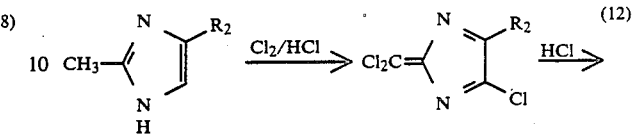
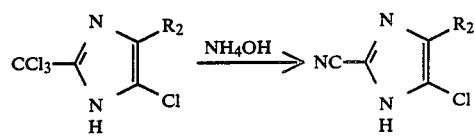
(12)
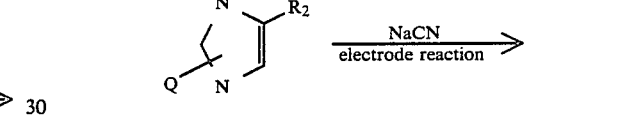
(13)
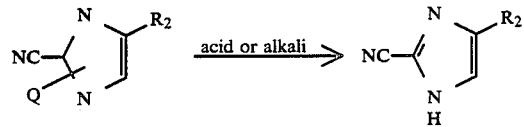
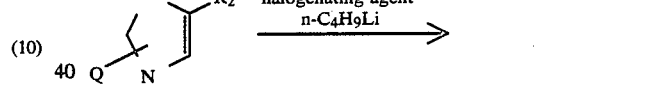
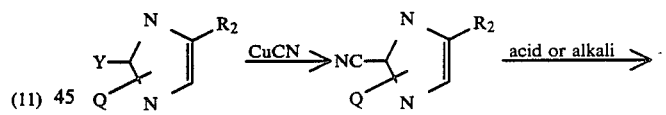
(14)
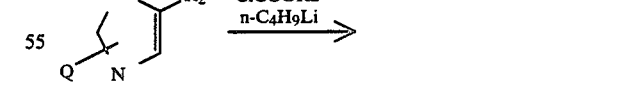
(15)
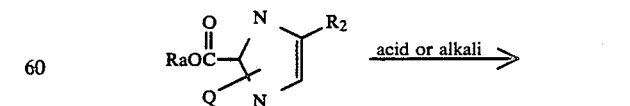
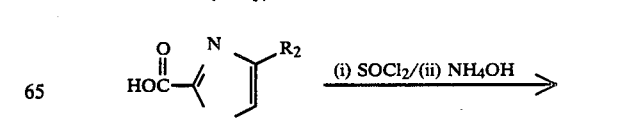

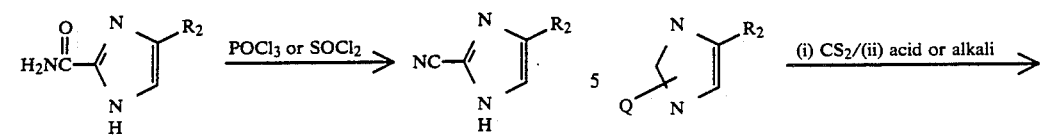
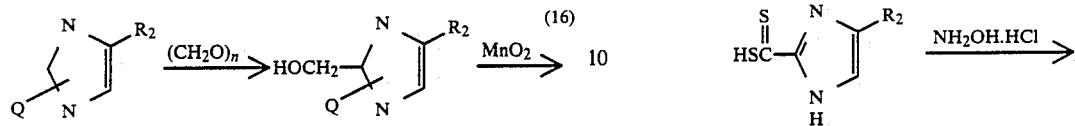
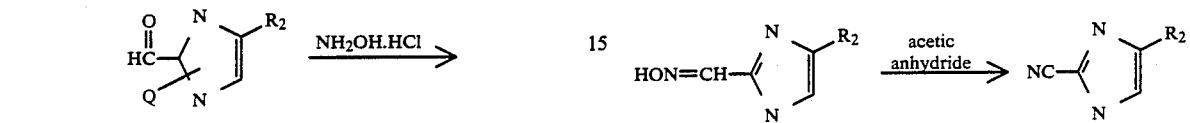
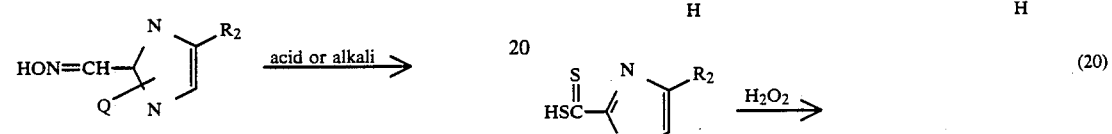
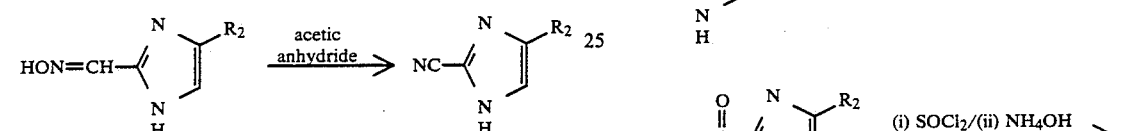
(16)
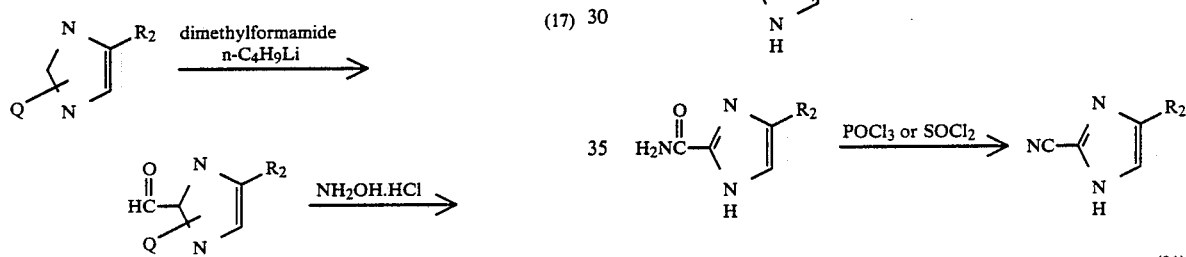
(17)
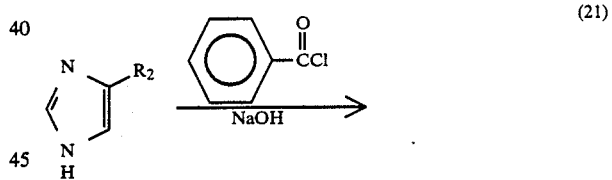
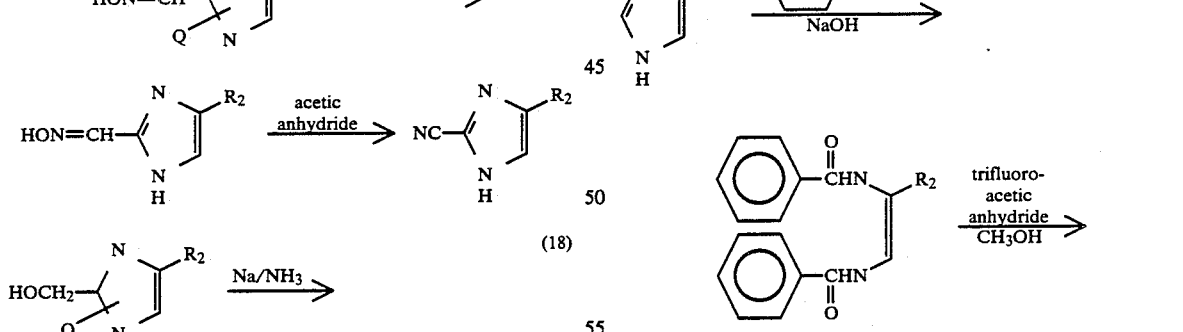
(18)
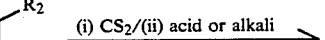
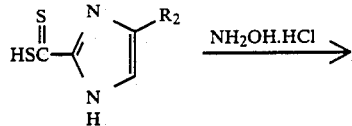
(19)
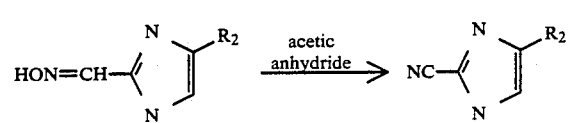
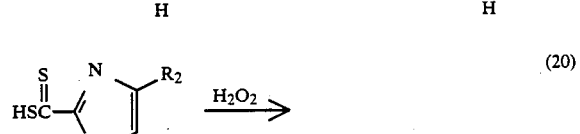
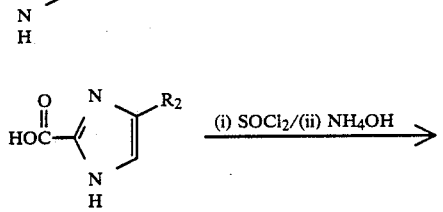
(20)
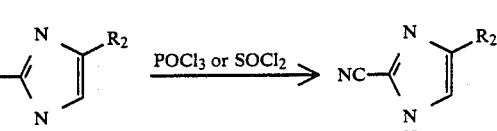
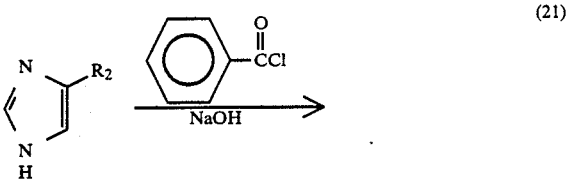
(21)
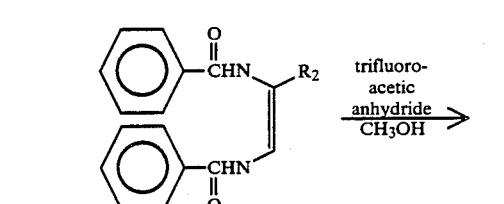
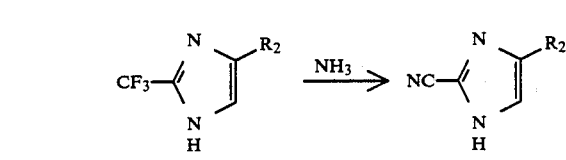
(22)
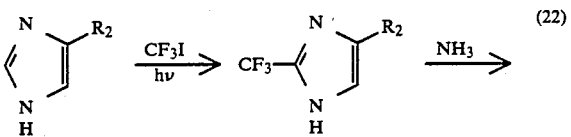

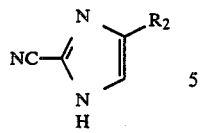

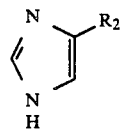

In the foregoing formulae, $R_2$, $R_3$, $R_4$, $R_5$, and Y have the same meanings as described above; X is a $CF_3$ group or a $CCl_3$ group; Ra is an alkyl group; and Q is a protective group.

As the protective groups for Q, an $-SO_2Rb$ group, wherein Rb is a dialkylamino group, an alkyl group, or an optionally alkylated phenyl group; a $-CH(Rc)-Rd$ group, wherein Rc is a hydrogen atom or a methyl group, and Rd is an alkoxy group, a phenyl group which is optionally substituted with an alkyl group or an alkoxy group, or a $-OC_2H_4Si(CH_3)_3$, etc. are exemplified.

In each of the processes as described above, the reaction conditions such as reaction temperature, reaction time, solvent, acid acceptor, alkali acceptor, etc. can appropriately be chosen from the conventionally known reaction conditions.

Further, the compounds of the formula

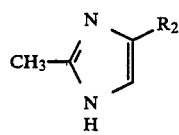

in the reaction schemes of the processes (10), (11), and (12) described above can be prepared by, for example, the following methods:

(23) 
R_2-CO-CH_2-A_1 or R_2-CH(A_1)-CHO → CH_3-A_2

(24)
R_2-CO-CHO → CH_3-A_4 / NH_3

(25)
R_2-CH(NH_2)-CH_2-NH_2 → CH_3-A_4 → CH_3-[imidazoline with R_2] → oxidation

(26)
CH_3-[imidazole N-OH with R_2] → TiCl_3

Still further, the compounds of the formula in the reaction schemes of the processes (13), (21), and (22) described above can be prepared by, for example, the following methods:

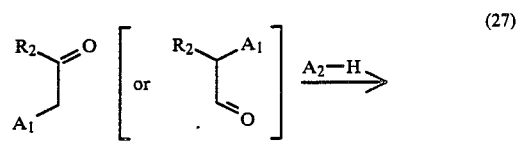

(27)

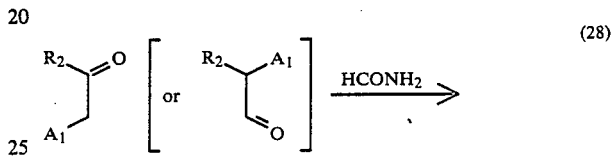

(28)

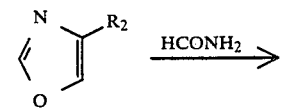

(29)

(30)
R_2-CO-CH_2-A_1 or R_2-CH(A_1)-CHO → guanidine

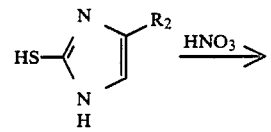

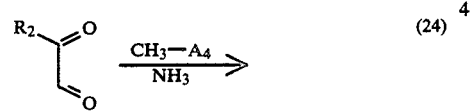

(31)
R_2-CO-CHO → A_4-H / NH_3

(32)
R_2-CH(NH_2)-CH_2-NH_2 → A_4-H → [imidazoline] → oxidation

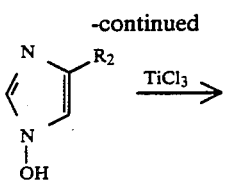

In the foregoing formulae, $R_2$ has the same meanings as described above; $A_1$ is a halogen atom, an amino group, a hydroxyl group, or an alkanoyloxy group; $A_2$ is a —$CONH_2$ group, a —$C(NH)NH_2$ group, or a —$C(NH)$—$A_3$ group, wherein $A_3$ is an alkoxy group or an alkylthio group; and $A_4$ is a formyl group.

The carbonyl group included in the above described formulae may be in the latent form of, for example, acetal, thioacetal, cyclic acetal, cyclic thioacetal, etc. Further, the formyl group represented by $A_4$ may be in the latent form of, for example, acetal, hemiacetal, etc.

In each of the processes as described above, the reaction conditions such as reaction temperature, reaction time, solvent, acid acceptor, alkali acceptor, etc. can appropriately be chosen from the conventionally known reaction conditions.

Typical examples of the intermediate compounds represented by the general formula (II), for the imidazole compounds of the present invention represented by the general formula (I) are shown in Table 1.

TABLE 1

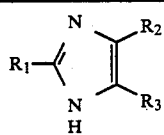
(II)

| Intermediate No. | $R_1$ | $R_2$ | $R_3$ | Melting Point (°C.) |
|---|---|---|---|---|
| 1 | CN | Br | H | 196–201 |
| 2 | " | 3-trifluoromethylphenyl | " | 160–168 |
| 3 | " | Cl | $CH_3$ | 194–196 |
| 4 | " | 4-methoxyphenyl | Cl | 150–155 |
| 5 | " | phenyl | $CH_3$ | 222–225 |
| 6 | " | " | Br | 120–125 |
| 7 | " | 4-fluorophenyl | H | 211–213 |
| 8 | " | 4-methylphenyl | " | 228–232 |
| 9 | " | " | Br | 142–144 |
| 10 | " | 4-fluorophenyl | " | 176–178 |
| 11 | " | 3,4-dichlorophenyl | H | 115–121 |
| 12 | " | 4-methylphenyl | Cl | 124–129 |
| 13 | " | Cl | H | 150–153 |
| 14 | " | n-$C_3H_7$ | Cl | 107–109 |
| 15 | " | phenyl | " | 149–151 |
| 16 | CN | 3-methylphenyl | Cl | 140–142 |
| 17 | " | 3,4-dimethylphenyl | " | 150–152 |
| 18 | " | 4-fluorophenyl | " | 153–155 |
| 19 | " | 4-bromophenyl | " | 162–167 |
| 20 | " | 4-ethylphenyl | " | 141–145 |
| 21 | " | " | H | 214–217 |
| 22 | " | 3-methoxyphenyl | " | 218–220 |
| 23 | " | 4-nitrophenyl | " | 230–235 |
| 24 | " | 5-chloro-2-thienyl | " | 202–206 |
| 25 | " | $SCH_3$ | " |  |
| 26 | " | phenylthio | " | 166–169 |
| 27 | " | phenyl | CN | 207–215 |
| 28 | " | H | F |  |
| 29 | " | 2-naphthyl | Cl | 146–149 |
| 30 | " | " | H | 253–255 |
| 31 | " | 4-nitrophenyl | Cl | 189–191 |
| 32 | " | 4-chlorophenyl | H | 215–224 |
| 33 | " | 4-chlorophenyl | Cl | 178–181 |
| 34 | " | 2-chlorophenyl | " | 145–152 |
| 35 | " | " | Br | 152–156 |
| 36 | " | 4-isopropylphenyl | H | 180–184 |

TABLE 1-continued

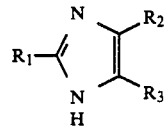
(II)

| Intermediate No. | $R_1$ | $R_2$ | $R_3$ | Melting Point (°C.) |
|---|---|---|---|---|
| 37 | " | 4-methylthiophenyl | " | 217–219 |
| 38 | CN | 4-(2',2', 2'-trifluoroethoxy)phenyl | H | 195–198 |
| 39 | " | $CH_3$ | $NO_2$ | 125–130 |
| 40 | " | tert-$C_4H_9$ | Br | 120–127 |
| 41 | " | 2-methylphenyl | H |  |
| 42 | " | " | Cl |  |
| 43 | " | 5-methyl-2-furyl | H | 169–171 |
| 44 | " | 3,4-dimethoxyphenyl | " | 188–190 |
| 45 | " | 4-ethoxyphenyl | " | 218–219 |
| 46 | " | 3-methyl-4-methoxyphenyl | " | 199–205 |
| 47 | " | 2-thienyl | " | 195–203 |
| 48 | " | 4-(2',2',2'-trifluoroethoxy)phenyl | Cl | 164–166 |
| 49 | " | " | Br | 150–155 |
| 50 | " | 3-methyl-4-methoxyphenyl | Cl | 145–149 |
| 51 | " | 3-chloro-4-methylphenyl | Br | 190–194 |
| 52 | " | $CH_3$ | CN | 142–145 |
| 53 | " | $C_2H_5$ | H | 127–129 |
| 54 | " | " | Cl | 138–140 |
| 55 | " | n-$C_3H_7$ | H | 52–54 |
| 56 | " | " | I | 106–109 |
| 57 | " | n-$C_4H_9$ | H | 83–85 |
| 58 | CN | n-$C_4H_9$ | Cl | 107–109 |
| 59 | " | n-$C_5H_{11}$ | H | 89–92 |
| 60 | " | n-$C_5H_{11}$ | Cl | 109–110 |
| 61 | " | iso-$C_3H_7$ | H | 88–91 |
| 62 | " | " | Cl | 84–87 |
| 63 | " | iso-$C_4H_9$ | H |  |
| 64 | " | " | Cl | 142–145 |
| 65 | " | tert-$C_4H_9$ | H | 130–135 |
| 66 | " | " | Cl | 120–124 |
| 67 | " | iso-$C_5H_{11}$ | H | 144–146 |
| 68 | " | " | Cl | 104–107 |
| 69 | " | cyclopropyl | " | 170–183 |
| 70 | " | cyclohexyl | H | 185–190 |
| 71 | " | " | Cl | 130—133 |
| 72 | " | 3-chloropropyl | " | 117–120 |
| 73 | " | $CH_2OCH_3$ | " |  |
| 74 | " | $CH_2OC_2H_5$ | " |  |
| 75 | " | benzyl | " | 144–146 |
| 76 | " | phenethyl | " | 147–152 |
| 77 | " | $SC_2H_5$ | H | 112–115 |
| 78 | " | " | Cl | 128–131 |
| 79 | " | S-n-$C_4H_9$ | H | 97–99 |
| 80 | " | " | Cl | 95–99 |
| 81 | CN | 3-fluoropropyl | Cl |  |
| 82 | " | $SO_2N(CH_3)_2$ | H | 175–180 |
| 83 | " | 3-chlorophenyl | " | 140–143 |
| 84 | " | " | Cl | 124–128 |
| 85 | " | 2,3-dichlorophenyl | H | 202–206 |
| 86 | " | " | Cl | 198–204 |
| 87 | " | 3-chloro-4-methoxyphenyl | " | 158–160 |
| 88 | " | " | Br | 161–163 |
| 89 | " | 3-chloro-4-methylphenyl | Cl | 165–169 |
| 90 | " | 4-cyanophenyl | H | 240–244 |
| 91 | " | " | Cl | 250–255 |
| 92 | " | " | Br | 239–244 |
| 93 | " | 4-ethoxyphenyl | Cl | 151–153 |
| 94 | " | " | Br | 140–145 |
| 95 | " | 2-fluorophenyl | H | 190–195 |
| 96 | " | " | Cl | 155–159 |
| 97 | " | 2-methoxyphenyl | H | 155–159 |
| 98 | " | " | Cl | 223–230 |
| 99 | " | 3,4-methylenedioxyphenyl | H | 228–231 |
| 100 | " | " | Cl | 149–152 |

TABLE 1-continued

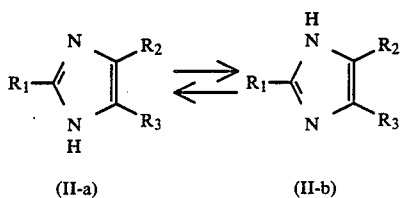

| Intermediate No. | $R_1$ | $R_2$ | $R_3$ | Melting Point (°C.) |
|---|---|---|---|---|
| 101 | " | " | Br | 166–169 |

In the case that $R_2$ and $R_3$ are different from each other, the intermediate compounds represented by the general formula (II) described above include tautomers represented by the general formulae (II-a) and (II-b) described below:

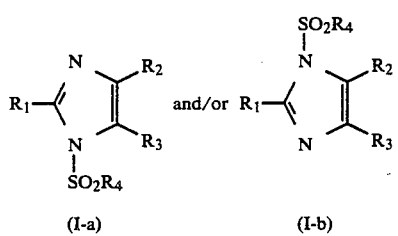

(II-a)   (II-b)

wherein $R_1$, $R_2$, and $R_3$ have the same meanings as described hereinabove. Accordingly, in the case that the imidazole compounds of the present invention represented by the general formula (I) are prepared using the compounds represented by the general formula (II) as a starting material, the imidazole compounds represented by the general formulae (I-a) and/or (I-b) described below can be obtained.

(I-a)   (I-b)

$R_1$, $R_2$, $R_3$, and $R_4$ have the same meanings as described hereinabove. In the case that $R_2$ and $R_3$ are different from each other, the imidazole compounds represented by the general formulae (I-a) and (I-b) are tautomers each other. The same also applies to the compounds represented by the general formulae (I-1), (I-5), (I-6), and (I-7) in the processes [B] to [D] described hereinabove, etc.

The imidazole compounds represented by the general formula (I-a) or (I-b) described hereinabove can be separated concretely, for example, by methods [E-1] to [E-3] described below:

[E-1] Method by means of chromatography

Each compound can be separated from a mixture of isomers of the general formulae (I-a) and (I-b) described above, by means of silica gel column chromatography, preparative high performance liquid chromatography, flash chromatography, etc. In the case of silica gel column chromatography, for example, n-hexane, carbon tetrachloride, methylene chloride, chloroform, ethyl acetate, or a mixture thereof can be used as a developing solvent.

[E-2] Method by means of recrystallization

Each compound can be separated from a mixture of isomers of the general formulae (I-a) and (I-b) described above, using as a solvent for recrystallization, for example, carbon tetrachloride, methylene chloride, chloroform, 1,2-dichloroethane, ethyl acetate, diethyl ether, tetrahydrofuran, acetone, or a mixture thereof.

[E-3] Method by means of decomposition

Either compound can be separated from a mixture of isomers of the general formulae (I-a) and (I-b) described above, by the selective hydrolysis under conditions of from 0° to 80° C. (preferably from room temperature to 50° C.) for from 1 to 48 hours (preferably from 5 to 24 hours).

As the mixture of isomers used in the methods [E-1] to [E-3] described above, it is preferred to use the mixture having a mixing ratio of both isomers as large as possible by appropriately choosing reaction conditions previously in the process [A] described above, for example, kind of solvent and acid acceptor and amounts thereof to be used, reaction temperature, reaction time, etc.

Further, in the case of preparing imidazole compounds wherein $R_1$ is a —$CSNH_2$ group or a —$CSNHR_5$ group, wherein $R_5$ has the same meaning as described hereinabove from compounds wherein $R_1$ is a cyano group in the compounds represented by the general formula (I-b) separated by the method [E-1], [E-2], or [E-3] described above, such compounds can be obtained, for example, by the following method:

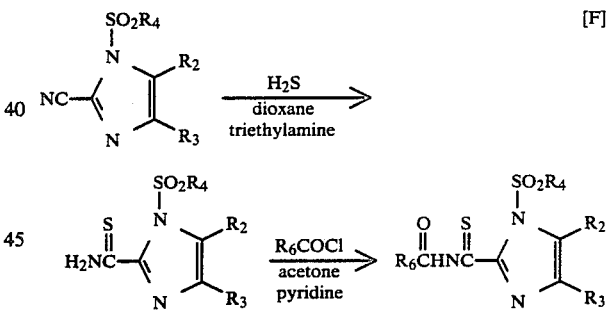

[F]

wherein $R_2$, $R_3$, $R_4$, and $R_6$, have the same meanings as described hereinabove.

Specific examples of synthesizing the imidazole compounds of the present invention are described below.

SYNTHESIS EXAMPLE 1

Synthesis of 2-cyano-1-dimethylsulfamoylimidazole (Compound No. 1)

Thirty grams of 2-cyanoimidazole, 53.4 g of anhydrous potassium carbonate and 600 ml of acetonitrile were mixed at room temperature. After reacting for 2 hours at the refluxing temperature, the reaction mixture was cooled, and 55.6 g of dimethylsulfamoyl chloride was added thereto. The mixture was reacted again at the refluxing temperature for 2 hours.

After completion of the reaction, the reaction mixture was poured into water. Extraction with methylene chloride was carried out. After washing with water, the extract was dried over anhydrous sodium sulfate. The solvent was removed by distillation. The obtained residue was purified by silica gel column chromatography (developing solvent: methylene chloride) to give 28.0 g of 2-cyano-1-dimethylsulfamoylimidazole (Compound No. 1) having a melting point of from 74° to 76° C.

SYNTHESIS EXAMPLE 2

Synthesis of
2-cyano-1-dimethylsulfamoyl-5-phenylthioimidazole
(Compound No. 10-b)

In a four-necked flask were charged 12.0 g of 2-cyano-1-dimethylsulfamoylimidazole (Compound No. 1) and 240 ml of dry tetrahydrofuran in a nitrogen flow. While maintaining the mixture at −75° C. or below with dry ice-acetone, 41.3 ml of a 1.6 M n-butyl lithium hexane solution (manufactured by Aldrich) was gradually added dropwise to the mixture. After completion of the dropwise addition, the system was kept at the same temperature for 15 minutes. Then, a solution of 17 g of diphenyl disulfide in 30 ml of tetrahydrofuran was added dropwise to the mixture at −70° C. or below. While stirring overnight, the temperature was gradually reverted to room temperature.

After completion of the reaction, the reaction mixture was poured into water. Extraction with 500 ml of ethyl acetate was carried out. After washing with water, the extract was dried over anhydrous sodium sulfate. The ethyl acetate was removed by distillation, and the residue was purified by silica gel column chromatography (developing solvent: methylene chloride) to give 4.3 g of 2-cyano-1-dimethylsulfamoyl-5-phenylthioimidazole (Compound No. 10-b) having a melting point of from 106° to 107° C.

SYNTHESIS EXAMPLE 3

Synthesis of
4-chloro-2-cyano-1-dimethylsulfamoyl-5-n-propylimidazole (Compound No. 16-b)

[1] 4.8 g of 2-cyano-1-dimethylsulfamoyl-5-n-propylimidazole having a melting point of from 51° to 52° C. (Compound No. 3-b) was synthesized by the reaction of 12.0 g of 2-cyano-1-dimethylsulfamoylimidazole (Compound No. 1) and 15.3 g of n-propyl iodide in a manner similar to Synthesis Example 2 described above.

[2] 4.8 g of 2-cyano-1-dimethylsulfamoyl-5-n-propylimidazole as obtained in [1] above, 40 ml of pyridine, and 11.4 g of pyridinium chloride were mixed, and the mixture was stirred at 90° C. for 4 hours. After completion of the reaction, the pyridine was removed by distillation from the reaction mixture, and the residue was extracted with ethyl acetate. The extract was washed with water and then dried over anhydrous sodium sulfate. Thereafter, the ethyl acetate was removed by distillation, and the residue was purified by silica gel column chromatography (developing solvent: a mixture of ethyl acetate and n-hexane) and separated to give 2.46 g of 2-cyano-4(5)-n-propylimidazole (Intermediate No. 55) having a melting point of from 52° to 54° C.

[3] 2.35 g of 2-cyano-4(5)-n-propylimidazole as obtained in [2] above, 80 ml of chloroform, and 2.6 g of N-chlorosuccinimide were mixed, and the mixture was reacted at the refluxing temperature for 4 hours. After completion of the reaction, 200 ml of water was added to the reaction mixture. The resulting organic layer was washed with water and then dried over anhydrous sodium sulfate. After drying, the chloroform was removed by distillation, and the residue was purified by silica gel column chromatography (developing solvent: a 1:1 mixture of ethyl acetate and n-hexane) and separated to give 2.2 g of 4(5)-chloro-2-cyano-5(4)-n-propylimidazole (Intermediate No. 14) having a melting point of from 107° to 109° C.

[4] 2.0 g of 4(5)-chloro-2-cyano-5(4)-n-propylimidazole as obtained in [3] above, 30 ml of acetonitrile, 1.95 g of anhydrous potassium carbonate, and 1.86 g of dimethylsulfamoyl chloride were mixed, and after gradually elevating the temperature, the mixture was reacted at the refluxing temperature for 1 hours. After completion of the reaction, the acetonitrile was removed by distillation from the reaction mixture. After pouring 100 ml of water into the residue, the resulting mixture was extracted with 50 ml of methylene chloride. The extract was washed with water and dried over anhydrous sodium sulfate. Thereafter, the methylene chloride was removed by distillation. The residue was allowed to stand overnight, and the analysis thereof revealed that one of the two isomers in the mixture decomposed and returned to the starting 4(5)-chloro-2-cyano-5(4)-n-propylimidazole. The residue containing the other isomer was purified by silica gel column chromatography (developing solvent: methylene chloride) and separated to give 1.1 g of 4-chloro-2-cyano-1-dimethylsulfamoyl-5-n-propylimidazole (Compound No. 16-b) having a melting point of from 64° to 66° C.

SYNTHESIS EXAMPLE 4

Synthesis of
2-cyano-1-dimethylsulfamoyl-4(5)-phenylimidazole
(Compound No. 4)

[1] In 320 ml of acetone was dissolved 23.04 g of 4(5)-phenylimidazole, and 12.14 g of anhydrous potassium carbonate was added to the solution. The mixture was heated at the refluxing temperature for 2 hours. After cooling, 45 ml of an acetone solution containing 25.25 g of dimethylsulfamoyl chloride was added dropwise to the mixture. After completion of the dropwise addition, the mixture was heated at the refluxing temperature for 4.5 hours to complete the reaction.

After completion of the reaction, the reaction mixture was cooled, and solid substances were removed by filtration. After the solvent was removed by distillation under reduced pressure, the residue was purified by silica gel column chromatography (developing solvent: methylene chloride) to give 17.8 g of 1-dimethylsulfamoyl-4(5)-phenylimidazole having a melting point of from 96° to 100° C.

[2] In 290 ml of tetrahydrofuran was dissolved 17 g of 1-dimethylsulfamoyl-4(5)-phenylimidazole as obtained in [1] above. The solution was cooled to −70° C. in a nitrogen flow, and 51 ml of a 1.6 M n-butyl lithium hexane solution was added dropwise to the mixture over 30 minutes. After completion of the dropwise addition, the reaction mixture was stirred at −70° C. for 30 minutes. Then, 12 ml of a tetrahydrofuran solution containing 6 g of N,N-dimethylformamide was added dropwise to the mixture. After completion of the dropwise addition, the reaction mixture was reacted for 15 hours with stirring while slowly elevating the temperature to room temperature.

After completion of the reaction, the reaction mixture was poured into ice water and extracted with ethyl acetate. After washing the extracted layer with water, the extracted layer was dried over anhydrous sodium sulfate. The solvent was distilled off under reduced pressure, and the residue was purified by silica gel column chromatography (developing solvent: a 1:2 mixture of ethyl acetate and n-hexane) to give 12.8 g of 1-dimethylsulfamoyl-2-formyl-4(5)-phenylimidazole having a melting point of from 86° to 89° C.

[3] In 120 ml of pyridine were dissolved 11.16 g of 1-dimethylsulfamoyl-2-formyl-4(5)-phenylimidazole as obtained in [2] above and 5.56 g of hydroxylamine hydrochloride, and 24 ml of acetic anhydride was added dropwise to the solution at room temperature. After completion of the dropwise addition, the temperature was gradually raised, and the mixture was reacted at 100° C. for 12 hours.

After completion of the reaction, the solvent in the reaction mixture was removed by distillation under reduced pressure. Then, 125 ml of water was added to the residue, and the precipitated solid was separated by filtration. The crude produce was dissolved in ethyl acetate and purified by silica gel column chromatography (developing solvent: ethyl acetate) to give 5.55 g of 2-cyano-4(5)-phenylimidazole having a melting point of from 203° to 205° C.

[4] In 88 ml of acetone was dissolved 1.7 g of 2-cyano-4(5)-phenylimidazole as obtained in [3] above, and 1.7 g of anhydrous potassium carbonate was added to the solution. The mixture was heated at the refluxing temperature for 2 hours.

After cooling, 6 ml of an acetone solution containing 1.7 g of dimethylsulfamoyl chloride was added dropwise to the mixture. After completion of the dropwise addition, the mixture was heated at the refluxing temperature for 2 hours to complete the reaction.

After completion of the reaction, the reaction mixture was cooled, and solid substances were removed by filtration. After the solvent was removed by distillation under reduced pressure, the residue was extracted with ethyl acetate. The extract was washed with water and dried over anhydrous sodium sulfate. The solvent was removed by distillation under reduced pressure to give 2 g of 2-cyano-1-dimethylsulfamoyl-4(5)-phenylimidazole (Compound No. 4) having a melting point of from 101° to 102° C.

SYNTHESIS EXAMPLE 5

Synthesis of 4(5)-chloro-2-cyano-1-dimethylsulfamoyl-5(4)-phenylimidazole (Compound No. 17) and 4-chloro-2-cyano-1-dimethylsulfamoyl-5-phenylimidazole (Compound No. 17-b)

[1] In 100 ml of chloroform was dissolved 1.352 g of 2-cyano-4(5)-phenylimidazole, and 1.175 g of N-chlorosuccinimide was added to the solution. The mixture was reacted upon heating at the refluxing temperature for 4 hours.

After completion of the reaction, the reaction mixture was poured into water and extracted with chloroform. After washing with water, the extracted layer was dried over anhydrous sodium sulfate. The solvent was distilled off under reduced pressure, and the residue was purified by silica gel column chromatography (developing solvent: methylene chloride) to give 1.28 g of 4(5)-chloro-2-cyano-5(4)-phenylimidazole (Intermediate No. 15) having a melting point of from 149° to 151° C.

[2] In 6 ml of acetone was dissolved 0.43 g of 4(5)-chloro-2-cyano-5(4)-phenylimidazole as obtained in [1] above, and 0.29 g of anhydrous potassium carbonate and 0.36 g of dimethylsulfamoyl chloride were added to the solution. The mixture was reacted upon heating at the refluxing temperature for 30 minutes.

After completion of the reaction, the reaction mixture was poured into water and extracted with ethyl acetate. After washing with water, the extracted layer was dried over anhydrous sodium sulfate. The solvent was distilled off under reduced pressure, and the residue was then purified by silica gel column chromatography (developing solvent: methylene chloride to give 0.5 g of 4(5)-chloro-2-cyano-1-dimethylsulfamoyl-5(4)-phenylimidazole (Compound No. 17) having a melting point of from 106° to 109° C.

As a result of analysis by means of NMR spectra, the compound described above was an isomer mixture of 4-chloro-2-cyano-1-dimethylsulfamoyl-5-phenylimidazole and 5-chloro-2-cyano-1-dimethylsulfamoyl-4-phenylimidazole in almost equal ratios.

[3] After allowing to stand for 24 hours at room temperature, 2.9 g of the mixture of these isomers as obtained in a manner similar to [2] above was purified by silica gel column chromatography (developing solvent: methylene chloride) to give 1.15 g of 4-chloro-2-cyano-1-dimethylsulfamoyl-5-phenylimidazole (Compound No. 17-b) having a melting point of from 109° to 112° C. Further, by purification of and isolation from this compound, 0.7 g of 4(5)-chloro-2-cyano-5(4)-phenylimidazole (Intermediate No. 15) was also obtained.

SYNTHESIS EXAMPLE 6

Synthesis of 4(5)-chloro-2-cyano-1-dimethylsulfamoyl-5(4)-(4-methylphenyl)imidazole (Compound No. 18) and 4-chloro-2-cyano-1-dimethylsulfamoyl-5-(4-methylphenyl)imidazole (Compound No. 18-b)

An isomer mixture (Compound No. 18), having a melting point of from 101° to 108° C., of 4-chloro-2-cyano-1-dimethylsulfamoyl-5-(4-methylphenyl)imidazole and 5-chloro-2-cyano-1-dimethylsulfamoyl-4-(4-methylphenyl)imidazole was obtained from 4(5)-(4-methylphenyl)imidazole in a ratio of 6:4 in a manner similar to Synthesis Examples 4 and 5 described above. After 0.75 g of the isomer mixture was reacted at 40° C. for 8 hours, the reaction mixture was purified by silica gel column chromatography (developing solvent: methylene chloride) to give 0.45 g of 4-chloro-2-cyano-1-dimethylsulfamoyl-5-(4-methylphenyl)imidazole (Compound No. 18-b) having a melting point of from 133° to 134° C. Further, by purification of and isolation from this compound, 0.15 g of 4(5)-chloro-2-cyano-5(4)-(4-methylphenyl)imidazole (Intermediate No. 12) having a melting point of from 124° to 129° C. was also obtained.

SYNTHESIS EXAMPLE 7

Synthesis of 4(5)-chloro-5(4-chlorophenyl)-b 2-cyano-1-dimethylsulfamoylimidazole (Compound No. 23), 4-chloro-5-(4-chlorophenyl)-b 2-cyano-1-dimethylsulfamoylimidazole (Compound No. 23-b) and 5-chloro-4(4-chlorophenyl)-2-cyano-1-dimethylsulfamoylimidazole (Compound No. 23-a)

In a manner similar to Synthesis Examples 4 and 5 described above, 0.80 g of an isomer mixture (Compound No. 23), having a melting point of 108° C., of 4-chloro-5-(4-chlorophenyl)-2-cyano-1-dimethylsulfamoylimidazole and 5-chloro-4-(4-chlorophenyl)-2-cyano-1-dimethylsulfamoylimidazole was obtained from 4(5)-(4-chlorophenyl)imidazole. The isomer mixture was purified by silica gel column chromatography (developing solvent: methylene chloride). The eluate of the second fraction was concentrated and recrystallized from methylene chloride to give 0.16 g of 4-chloro-5-(4-chlorophenyl)-2-cyano-1-dimethylsulfamoylimidazole (Compound No. 23-b) having a melting point of from 117° to 120° C. Further, the eluate of the first fraction was likewise concentrated and recrystallized from methylene chloride to give 0.50 g of 5-chloro-4-(4-chlorophenyl)-2-cyano-1-dimethylsulfamoylimidazole (Compound No. 23-a) having a melting point of from 133° to 138° C.

SYNTHESIS EXAMPLE 8

Synthesis of 1-dimethylsulfamoyl-4(5)-phenylimidazole-2-carbothioamide (Compound No. 49)

In 30 ml of dioxane was dissolved 1.0 g of 2-cyano-1-dimethylsulfamoyl-4(5)-phenylimidazole (Compound No. 4), and 0.36 g of triethylamine was added to the solution. The mixture was heated to 40° to 50° C. while stirring, and a hydrogen sulfide gas was introduced thereinto for one hour and 25 minutes. Thereafter, the mixture was reacted at 40° to 50° C. for an additional 50 minutes.

After completion of the reaction, the reaction mixture was cooled, poured into water, and extracted with ethyl acetate. After washing with water, the extracted layer was dried over anhydrous sodium sulfate. The solvent was distilled off under reduced pressure, and the residue was purified by silica gel column chromatography (developing solvent: a 1:3 mixture of ethyl acetate and n-hexane) to give 0.8 g of 1-dimethylsulfamoyl-4(5)-phenylimidazole-2-carbothioamide (Compound No. 49) having a melting point of from 155° to 175° C. Crystals of 4(5)-phenylimidazole-2-carbothioamide were also obtained in a small quantity.

SYNTHESIS EXAMPLE 9

Synthesis of 2-cyano-1-isopropylsulfonyl-4(5)-phenylimidazole (Compound No. 101)

One gram of 2-cyano-4(5)-phenylimidazole, 0.98 g of anhydrous potassium carbonate, and 30 ml of acetonitrile were mixed at room temperature. After reacting for 2 hours at the refluxing temperature, the reaction mixture was cooled, and a solution of 1.0 g of isopropylsulfonyl chloride in 5 ml of acetonitrile was added thereto. The mixture was reacted again at the refluxing temperature for 1.5 hours.

After completion of the reaction, the reaction mixture was poured into water. Extraction with methylene chloride was carried out. After washing with water, the extract was dried over anhydrous sodium sulfate. The solvent was removed by distillation under reduced pressure, and the residue was purified by silica gel column chromatography (developing solvent: methylene chloride) to give 1.4 g of 2-cyano-1-isopropylsulfonyl-4(5)-phenylimidazole (Compound No. 101) having a melting point of from 80° to 83° C.

SYNTHESIS EXAMPLE 10

Synthesis of 4(5)-(2-thienyl)-2-cyano-1-dimethylsulfamoylimidazole (Compound No. 6)

[1] To 150 ml of formamide was added 25 g of 2-(bromoacetyl)thiophene. The mixture was reacted at 180° to 190° for 2 hours.

After completion of the reaction, the reaction mixture was poured into water, and concentrated hydrochloric acid was added thereto to render the system acidic. Then, washing with methylene chloride was carried out. After neutralizing with ammonia water, the aqueous phase was extracted with methylene chloride. After washing with water, the extract was dried over anhydrous sodium sulfate. The solvent was removed by distillation under reduced pressure to give 11 g of 4(5)-(2-thienyl)imidazole.

[2] To 200 ml of acetonitrile were added 11.6 g of dimethylsulfamoyl chloride, 11.1 g of anhydrous potassium carbonate, and 11 g of 4(5)-(2-thienyl)imidazole as obtained in [1] above. The mixture was reacted for 2 hours while stirring.

After completion of the reaction, the reaction mixture was poured into water. Extraction with ethyl acetate was carried out. After washing with water, the extract was dried over anhydrous sodium sulfate. The solvent was removed by distillation under reduced pressure to give 14.5 g of 4(5)-(2-thienyl)-1-dimethylsulfamoylimidazole.

[3] In 120 ml of anhydrous tetrahydrofuran was dissolved 9.5 g of 4(5)-(2-thienyl)-1-dimethylsulfamoylimidazole as obtained in [2] above. In a nitrogen flow, 26.2 ml of a 1.6 M n-butyl lithium hexane solution was added dropwise to the solution at −78° C., and the mixture was stirred at the same temperature for 15 minutes. Then, 20 ml of a tetrahydrofuran solution having dissolved therein 5.4 g of N,N-dimethylformamide was added dropwise to the mixture. After completion of the dropwise addition, the temperature was gradually reverted to room temperature to complete the reaction.

After completion of the reaction, the reaction mixture was poured into water. Extraction with ethyl acetate was carried out. After washing with water, the extract was dried over anhydrous sodium sulfate. The solvent was removed by distillation under reduced pressure to give 5.4 g of 4(5)-(2-thienyl)-2-formyl-1-dimethylsulfamoylimidazole.

[4] In 54 ml of pyridine were dissolved 2.6 g of hydroxylamine hydrochloride and 5.4 g of 4(5)-(2-thienyl)-2-formyl-1-dimethylsulfamoylimiazole as obtained in [3] above. The solution was stirred at room temperature for 15 minutes. Then, 10 ml of acetic anhydride was gradually added to the solution, followed by reacting at 60° to 70° C. for 2 hours.

After completion of the reaction, the reaction mixture was poured into water. Extraction with ethyl acetate was carried out. After washing with water, the extract wad dried over anhydrous sodium sulfate. The solvent was removed by distillation under reduced pressure, and the residue was purified by silica gel column chromatography (developing solvent: a 2:1 mixture of ethyl acetate and n-hexane) to give 1.2 g of 4(5)-(2-thienyl)-2-cyanoimiazole (Intermediate No. 47) having a melting point of from 195° to 203° C.

[5] To 5 ml of acetonitrile were added 1.1 g of dimethylsulfamoyl chloride, 1.0 g of anhydrous potassium carbonate, and 1.2 g of 4(5)-(2-thienyl)-2-cyanoimidazole as obtained in [4] above. The mixture was reacted at the refluxing temperature of 2 hours.

After completion of the reaction, the reaction mixture was poured into water and extracted with ethyl acetate. After drying the extract over anhydrous sodium sulfate, the solvent was distilled off under reduced pressure, and the residue was purified by silica gel column chromatography (developing solvent: methylene chloride) to give 1.3 g of 4(5)-(2-thienyl)-2-cyano-1-dimethylsulfamoylimidazole (Compound No. 6) having a melting point of from 145° to 150° C.

SYNTHESIS EXAMPLE 11

Synthesis of 4(5)-chloro-2-cyano-1-dimethylsulfamoyl-5(4)-isopropylimidazole (Compound No. 125) and 4-chloro-2-cyano-1-dimethylsulfamoyl-5-isopropylimidazole (Compound No. 125-b)

[1] 360 g of formamide was heated to 180° C., and 102 g of 1-hydroxy-3-methyl-2-butanone (prepared in a manner as described in Lipshutz and Morey, J. Org. Chem., 48, 3745 (1983)) was added dropwise thereto over 30 minutes. After completion of the dropwise addition, the mixture was reacted at 180° C. for one hour.

After completion of the reaction, the reaction mixture was cooled and poured into ice water. The resulting mixture was adjusted at a pH of 1 with hydrochloric acid and washed with methylene chloride. The aqueous layer was adjusted at a pH of 4 to 5 with ammonia water. 5 g of activated charcoal was added thereto, and the mixture was stirred for one hour. The activated charcoal was removed by filtration, and the filtrate was adjusted at a pH of 8 with ammonia water. Then, extraction with methylene chloride was carried out, and the extract was dried over anhydrous sodium sulfate. The solvent was distilled off under reduced pressure to give 13 g of 4(5)-isopropylimidazole.

[2] In 300 ml of acetonitrile was dissolved 11.8 g of 4(5)-isopropylimidazole as obtained in [1] above, and 18 g of anhydrous potassium carbonate was added to the solution. The mixture was refluxed for 30 minutes, and after cooling, 17 g of dimethylsulfamoyl chloride was added dropwise thereto. After completion of the dropwise addition, the mixture was refluxed to complete the reaction.

After completion of the reaction, the reaction mixture was cooled, poured into water, and then extracted with ethyl acetate. The extracted layer was washed with water and dried over anhydrous sodium sulfate. The solvent was distilled off under reduced pressure, and the residue was purified by silica gel column chromatography (developing solvent: methylene chloride) to give 13 g of 1-dimethylsulfamoyl-4(5)-isopropylimidazole.

[3] In 200 ml of tetrahydrofuran was dissolved 13 g of 1-dimethylsulfamoyl-4(5)-isopropylimidazole as obtained in [2] above. The solution was cooled to −70° C. in a nitrogen flow, and 38 ml of a 1.6 M n-butyl lithium hexane solution was added dropwise thereto over 15 minutes. After completion of the dropwise addition, the mixture was stirred at −70° C. for 30 minutes. After dropwise addition of 5.6 of N,N-dimethylformamide, the mixture was reacted with stirring for 15 hours while slowly elevating the temperature to room temperature.

After completion of the reaction, the reaction mixture was poured into ice water and extracted with ethyl acetate. The extracted layer was washed with water and dried over anhydrous sodium sulfate. The solvent was distilled off under reduced pressure to obtain 8.6 g of 1-dimethylsulfamoyl-2-formyl-4(5)-isopropylimidazole.

[4] In 100 ml of pyridine was dissolved 8.5 g of 1-dimethylsulfamoyl-2-formyl-4(5)-isopropylimidazole as obtained in [3] above and 4.8 g of hydroxylamine hydrochloride, and 10 ml of acetic anhydride was added dropwise to the solution at room temperature. After completion of the dropwise addition, the temperature was gradually elevated, and the mixture was reacted at 80° to 90° C. for 5 hours.

After completion of the reaction, the solvent in the reaction mixture was distilled off under reduced pressure. To the residue was added water, and the mixture was extracted with ethyl acetate. The extracted layer was washed with dilute hydrochloric acid and then with water and dried over anhydrous sodium sulfate. The solvent was distilled off under reduced pressure to give 2.35 g of 2-cyano-4(5)-isopropylimidazole (Intermediate No. 61) having a melting point of from 88° to 91° C.

[5] In 80 ml of methanol was dissolved 2 g of 2-cyano-4(5)-isopropylimidazole as obtained in [4] above, and 2.1 g of N-chlorosuccinimide was added to the solution. The mixture was stirred at room temperature for 20 hours and then reacted at 40° C. for 8 hours.

After completion of the reaction, the methanol in the reaction mixture was distilled off under reduced pressure. To the residue was added water, and the mixture was extracted with ethyl acetate. The extracted layer was washed with water and dried over anhydrous sodium sulfate. The solvent was distilled off under reduced pressure, and the residue was purified by silica gel column chromatography (developing solvent: methylene chloride) to give 1.67 g of 4(5)-chloro-2-cyano-5(4)-isopropylimidazole (Intermediate No. 62) having a melting point of from 84° to 87° C.

[6] In 30 ml of acetonitrile was dissolved 1.6 g of 4(5)-chloro-2-cyano-5(4)-isopropylimidazole as obtained in [5] above, and 1.56 g of anhydrous potassium carboante was added to the solution. The mixture was refluxed for 30 minutes. After cooling, 1.49 g of dimethylsulfamoyl chloride was added dropwise thereto. After completion of the dropwise addition, the mixture was refluxed for 15 minutes to complete the reaction.

After completion of the reaction, the reaction mixture was cooled, poured into water, and then extracted with ethyl acetate. The extracted layer was washed with water and dried over anhydrous sodium sulfate. The solvent was distilled off under reduced pressure, and the residue was purified by silica gel column chromatography (developing solvent: methylene chloride) to give 2.1 g of 4(5)-chloro-2cyano-1-dimethylsulfamoyl-5(4)-isopropylimidazole (Compound No. 125).

As a result of analysis by means of NMR spectra, the compound described above was an isomer mixture of 4-chloro-2-cyano-1-dimethylsulfamoyl-5-isopropylimidazole and 5-chloro-2-cyano-1-dimethylsulfamoyl-4-isopropylimidazole in a proportion of about 2:1.

[7] After allowing to stand for 5 days at room temperature, 2.1 g of the isomer mixture as obtained in [6] above was purified by silica gel column chromatography (developing solvent: methylene chloride) to give 1 g of 4-chloro-2-cyano-1-dimethylsulfamoyl-5-isopropylimidazole (Compound No. 125-b) having a melting point of from 75° to 82° C. (decomposed). Further, by purification of and isolation from this compound, 4(5)-chloro-2-cyano-5(4)-isopropylimidazole (Intermediate No. 62) was also obtained.

SYNTHESIS EXAMPLE 12

Synthesis of 4-chloro-1-dimethylsulfamoyl-5-n-propylimidazole-2-carbothioamide (Compound No. 185-b)

[1] In a four-necked flask were charged 6.0 g of 2-cyano-4,5-dichloro-1-dimethylsulfamoylimidazole having a melting point of from 100° to 103° C. and 180 ml of dry tetrahydrofuran in a nitrogen flow. While maintaining the mixture at −75° C. or below with dry ice-acetone, 15.3 ml of a 1.6 M n-butyl lithium hexane solution (manufactured by Aldrich) was gradually added dropwise to the mixture. After completion of the dropwise addition, the system was kept at the same temperature for 15 minutes. Then, a solution of 5.7 g of n-propyl iodide in 15 ml of tetrahydrofuran was added dropwise to the mixture at −70° C. or below. While stirring overnight, the temperature was gradually reverted to room temperature.

After completion of the reaction, the reaction mixture was poured into water. Extraction with 500 ml of methylene chloride was carried out. After washing with water, the extract was dried over anhydrous sodium sulfate. The methylene chloride was removed by distillation, and the residue was purified by silica gel column chromatography (developing solvent: methylene chloride) and then again purified by silica gel column chromatography (developing solvent: a mixture of ethyl acetate and n-hexane) to give 2.8 g of 4-chloro-2-cyano-1-dimethylsulfamoyl-5-n-propylimidazole (Compound No. 16-b) having a melting point of from 66° to 68° C.

[2] In a four-necked flask were charged 2.7 g of 4 chloro-2-cyano-1-dimethylsulfamoyl-5-n-propylimidazole as obtained in [1] above, 40 ml of dioxane, 1.0 g of triethylamine, and 0.8 g of pyridine. Into this mixture was introduced a hydrogen sulfide gas at 20° to 25° C. for about 30 minutes until the starting materials had disappeared.

After completion of the reaction, the reaction mixture was poured into water, and precipitated crystals were filtered by means of a Nutsche and dried. The resulting crystals were purified by silica gel column chromatography (developing solvent: methylene chloride) and separated to give 2.3 g of 4-chloro-1-dimethylsulfamoyl-5-n-propylimidazole-2-carbothioamide (Compound No. 185-b) having a melting point of from 160° to 162° C.

SYNTHESIS EXAMPLE 13

Synthesis of N-propionyl-4-chloro-1-dimethylsulfamoyl-5-n-propylimidazole-2-carbothioamide (Compound No. 187-b)

Into a four-necked flask were charged 2.0 g of 4-chloro-1-dimethylsulfamoyl 5-n-propylimidazole-2-carbothioamide (Compound No. 185-b), 24 ml of acetone, and 1.12 g of pyridine. 1.19 g of propionyl chloride was added dropwise to the mixture at 0° to 5° C. After completion of the dropwise addition, the reaction was carried out at 30° to 35° C. for one hour and at the refluxing temperature for an additional 30 minutes with stirring.

After completion of the reaction, the reaction mixture was poured into water and extracted with ethyl acetate. The extracted layer was washed with water and dried over anhydrous sodium sulfate. Thereafter, the ethyl acetate was removed by distillation, and the residue was purified by silica gel column chromatography (developing solvent: methylene chloride) and separated to give 1.02 g of N-propionyl-4-chloro-1-dimethylsulfamoyl-5-n-propylimidazole-2-carbothioamide (Compound No. 187-b) having a melting point of from 150° to 152° C.

SYNTHESIS EXAMPLE 14

Synthesis of 2-cyano-1-dimethylsulfamoyl-4,5-diphenylthioimidazole (Compound No. 141)

[1] 8.0 g of 2-cyano-1-dimethylsulfamoyl-5-phenylthioimidazole (Compound No. 10-b) as obtained in a similar manner to Synthesis Example 2 described above, 60 ml of methanol, and 60 ml of a 7% hydrochloric acid aqueous solution were charged, and the mixture was reacted with stirring at 40° to 50° C. for 2 hours. After completion of the reaction, the reaction mixture was rendered weakly alkaline with ammonia, and precipitated crystals were separated by filtration and dried to give 4.2 g of 2-cyano-4(5)-phenylthioimidazole (Intermediate No. 26) having a melting point of from 166° to 169° C.

[2] To a mixture of 4.2 g of 2-cyano-4(5)-phenylthioimidazole as obtained in [1] above, 80 ml of acetonitrile, and 3.1 g of anhydrous potassium carbonate was added 3.4 g of dimethylsulfamoyl chloride. The resulting mixture was reacted at the refluxing temperature for one hour. After completion of the reaction, the reaction mixture was cooled, and solid substances were filtered. The solvent in the filtrate was removed by distillation, and the residue was purified by silica gel column chromatography (developing solvent: methylene chloride) and separated to give 5.8 g of 2-cyano-1-dimethylsulfamoyl-4(5)-phenylthioimidazole (Compound No. 10).

[3] In a four-necked flask were charged 5.8 g of 2-cyano-1-dimethylsulfamoyl-4(5)-phenylthioimidazole as obtained in [2] above and 150 ml of dry tetrahydrofuran in a nitrogen atmosphere, and 12.9 ml of a 1.6 M n-butyl lithium hexane solution (manufactured by Kanto Kagaku) was added dropwise to the mixture while maintaining the temperature at −75° C. or below with dry ice-acetone. After completion of the dropwise addition, the mixture was kept at the same temperature for 15 minutes, and 20 ml of a solution of 5.2 g of diphenyl disulfide in tetrahydrofuran was added dropwise thereto at −70° C. or below. Thereafter, the mixture was returned to room temperature. After completion of the reaction, the reaction mixture was extracted with ethyl acetate. The extract was washed with water and dried over anhydrous sodium sulfate. The solvent was removed by distillation, and the residue was purified by silica gel column chromatography (developing solvent: methylene chloride) and separated to give 1.7 g of 2-cyano-1-dimethylsulfamoyl-4,5-diphenylthioimidazole (Compound No. 141) having a melting point of from 98° to 101° C.

SYNTHESIS EXAMPLE 15

Synethsis of 4-bromo-2-cyano-1-dimethylsulfamoyl-5-n-propylimidazole (Compound No. 157-b)

[1] 2-Cyano-4,5-dibromo-1-dimethylsulfamoylimidazole having a melting point of from 118° to 120° C. was synthesized from 2-cyano-4,5-dibromoimidazole having a melting point of from 200° to 203° C. in a similar manner to Synthesis Example 1 described above.

[2] In a 200 ml four-necked flask were charged 5 g of 2-cyano-4,5-dibromo-1-dimethylsulfamoylimidazole as obtained in [1] above and 120 ml of dry tetrahydrofuran in a nitrogen flow. While maintaining the mixture at −75° C. or below with dry ice-acetone, 9.6 ml of a 1.6 M n-butyl lithium hexane solution (manufactured by Aldrich) was gradually added dropwise to the mixture. After completion of the dropwise addition, the system was kept at the same temperature for 15 minutes. Then, a solution of 3.6 g of n-propyl iodide in 15 ml of tetrahydrofuran was added dropwise to the mixture at −75° C. or below. While stirring, the temperature was gradually reverted to room temperature.

After completion of the reaction, the reaction mixture was extracted with ethyl acetate. After washing with water, the extract was dried over anhydrous sodium sulfate. The ethyl acetate was removed by distillation, and the residue was purified by silica gel column chromatography (developing solvent: methylene chloride) to give 2.1 g of 4-bromo-2-cyano-1-dimethylsulfamoyl-5-n-propylimidazole (Compound No. 157-b) having a melting point of from 93° to 94° C.

Typical examples of the imidazole compounds (general formula (I)) of the present invention are shown in Table 2.

TABLE 2

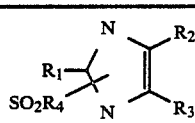

(I)

| Compound No. | $R_1$ | $R_2$ | $R_3$ | $R_4$ | Melting Point (°C.) |
|---|---|---|---|---|---|
| 1 | CN | H | H | —N(CH$_3$)$_2$ | 74–76 |
| 2 | " | CH$_3$ | " | " | 78–83 |
| 3 | " | n-C$_3$H$_7$ | " | " | |
| 4 | " | phenyl | " | " | 101–102 |
| 5 | " | 4-chlorophenyl | " | " | 148–149 |
| 6 | " | 2-thienyl | " | " | 145–150 |
| 7 | " | 5-chloro-2-thienyl | " | " | 145–148 |
| 8 | " | 5-bromo-2-thienyl | " | " | 138–140 |
| 9 | " | SCH$_3$ | " | " | |
| 10 | " | phenylthio | " | " | |
| 11 | " | 2-chlorophenyl | " | " | 118–121 |
| 12 | " | 4-nitrophenyl | " | " | 107–108 |
| 13 | " | 4-trifluoromethylphenyl | " | " | |
| 14 | " | H | Cl | " | |
| 15 | CN | CH$_3$ | Cl | —N(CH$_3$)$_2$ | |
| 16 | " | n-C$_3$H$_7$ | " | " | |
| 17 | " | phenyl | " | " | 106–109 |
| 18 | " | 4-methylphenyl | " | " | 101–108 |
| 19 | " | 3-methylphenyl | " | " | 90–95 |
| 20 | " | 2-methylphenyl | " | " | |
| 21 | " | 3,4-dimethylphenyl | " | " | 95–105 |
| 22 | " | 4-methoxyphenyl | " | " | 102–107 |
| 23 | " | 4-chlorophenyl | " | " | 108 |
| 24 | " | 2-chlorophenyl | " | " | |
| 25 | " | 3,4-dichlorophenyl | " | " | 99–105 |
| 26 | " | 4-fluorophenyl | " | " | 105–107 |
| 27 | " | SCH$_3$ | " | " | |
| 28 | " | phenylthio | " | " | |
| 29 | " | H | Br | " | |
| 30 | " | CH$_3$ | " | " | |
| 31 | " | tert-C$_4$H$_9$ | " | " | 88–90 |
| 32 | " | phenyl | " | " | |
| 33 | " | 4-methylphenyl | " | " | 106–108 |
| 34 | " | 4-tert-butylphenyl | " | " | 105–110 |
| 35 | " | 4-methoxyphenyl | " | " | 96–99 |
| 36 | CN | 4-fluorophenyl | Br | —N(CH$_3$)$_2$ | 87–93 |
| 37 | " | 4-chlorophenyl | " | " | |
| 38 | " | 1,2-dibromoethyl | Cl | " | |
| 39 | " | C$_2$H$_5$ | Br | " | |
| 40 | " | —CH$_2$CH=CH$_2$ | " | " | |
| 41 | " | 4-bromophenyl | Cl | " | 110–116 |
| 42 | " | 4-isopropylphenyl | " | " | |
| 43 | " | 2-naphthyl | " | " | 124–126 |
| 44 | " | CH$_3$ | CH$_3$ | " | 52–54 |
| 45 | " | phenyl | " | " | 101–105 |
| 46 | " | " | SCH$_3$ | " | |
| 47 | " | " | phenyl | " | 148–149 |
| 48 | " | " | CN | " | 124–129 |
| 49 | —CSNH$_2$ | phenyl | H | " | 155–175 |
| 50 | " | 4-chlorophenyl | " | " | 197–201 |
| 51 | " | phenyl | Cl | " | 110–130 |
| 52 | " | H | Br | " | 140–144 |
| 53 | " | phenyl | " | " | |
| 54 | CN | 3,4-dimethoxyphenyl | H | " | |
| 55 | " | 3-methyl-4-methoxyphenyl | Cl | " | |

TABLE 2-continued $$\begin{array}{c} \text{R}_1 \diagdown \diagup \text{N} = \text{C} \diagup \text{R}_2 \\ \text{SO}_2\text{R}_4 \diagup \diagdown \text{N} - \text{C} \diagdown \text{R}_3 \end{array} \quad (I)$$

| Compound No. | $R_1$ | $R_2$ | $R_3$ | $R_4$ | Melting Point (°C.) |
|---|---|---|---|---|---|
| 56 | CN | 4-ethylphenyl | Cl | —N(CH$_3$)$_2$ | |
| 57 | " | phenylthio | Br | " | |
| 58 | " | benzyl | " | " | |
| 59 | " | 3-chloropropyl | H | " | |
| 60 | " | —SO$_2$C$_2$H$_5$ | " | " | |
| 61 | " | 3-fluoropropyl | Cl | " | |
| 62 | " | 4-methylthiophenyl | H | " | |
| 63 | " | vinyl | Cl | " | |
| 64 | " | 5-methyl-2-thienyl | H | " | |
| 65 | " | 2-chlorophenyl | Br | " | |
| 66 | " | 3,4-dichlorophenyl | H | " | 139–142 |
| 67 | " | 4-(2′,2′,2′-trifluoroethoxy)phenyl | Cl | " | |
| 68 | " | 4-(2′,2′,2′-trifluoroethoxy)phenyl | Br | " | |
| 69 | " | —CH$_2$OH | H | " | |
| 70 | " | 3-chlorophenyl | Cl | " | |
| 71 | " | 3-fluorophenyl | " | " | |
| 72 | " | 2-fluorophenyl | " | " | 96–101 |
| 73 | " | —SCH$_2$CH=CH$_2$ | H | " | |
| 74 | " | CH$_3$ | NO$_2$ | " | 110–117 |
| 75 | CN | 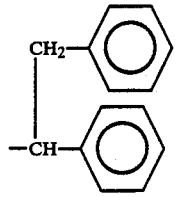 (1,2-diphenylethyl) | H | —N(CH$_3$)$_2$ | |
| 76 | " | 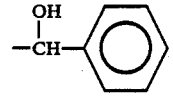 (α-hydroxybenzyl) | " | " | |
| 77 | " | (4-chloro-α-hydroxybenzyl) | " | " | |
| 78 | " | 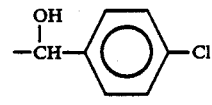 (4-chlorobenzoyl) | " | " | |
| 79 | " | acetyl | " | " | |
| 80 | 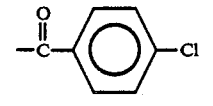 (N-acetylthiocarbamoyl) | phenyl | " | " | |
| 81 | $\overset{S}{\underset{\|}{-C}}\text{NH}\overset{O}{\underset{\|}{C}}\text{CH}_2\text{CH}_2\text{Cl}$ [N-(3-chloropropionyl)thiocarbamoyl] | " | " | " | |
| 82 | N-acetylthiocarbamoyl | CH$_3$ | H | —N(CH$_3$)$_2$ | |

TABLE 2-continued

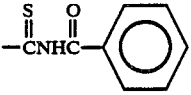
(I)

| Compound No. | R₁ | R₂ | R₃ | R₄ | Melting Point (°C.) |
|---|---|---|---|---|---|
| 83 | 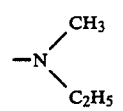<br>(N-benzoylthiocarbamoyl) | " | " | " | |
| 84 | CN | 5-methyl-2-furyl | " | " | 120–124 |
| 85 | " | $C_2H_5$ | Cl | 1-piperidinyl | |
| 86 | " | " | " | phenyl | |
| 87 | " | 4-(chloromethylthio)phenyl | H | $-N(CH_3)_2$ | 142–146 |
| 88 | " | $CH_3$ | CN | " | 80–84 |
| 89 | " | cyclohexyl | H | " | |
| 90 | " | $-SO_2CH_3$ | " | " | |
| 91 | " | 4-chlorobenzenesulfonyl | " | " | |
| 92 | " | phenyl | Cl | $C_2H_5$ | |
| 93 | " | " | " | cyclohexyl | |
| 94 | " | " | " | $CF_3$ | |
| 95 | " | " | " | 2-thienyl | |
| 96 | " | " | " | $-N\begin{matrix}CH_3\\C_2H_5\end{matrix}$ | |
| 97 | CN | phenyl | Cl | $-N\begin{matrix}CH_3\\CH_2CF_3\end{matrix}$ | |
| 98 | " | " | " | $-N\begin{matrix}CH_3\\CH_2CH=CH_2\end{matrix}$ | |
| 99 | " | " | " | 1-pyrrolidinyl | |
| 100 | " | 4-methylphenyl | " | morpholino | |
| 101 | " | phenyl | H | isopropyl | 80–83 |
| 102 | " | " | Cl | " | |
| 103 | " | " | " | $-N(C_2H_5)_2$ | 70–80 |
| 104 | " | " | Br | " | 55–76 |
| 105 | " | " | Cl | morpholino | 106–110 |
| 106 | " | " | Br | " | 70–83 |
| 107 | " | " | Cl | thiomorpholino | |
| 108 | " | 4-(2'-chloroethyl)phenyl | " | $-N(CH_3)_2$ | |
| 109 | " | 4-chlorobenzyl | Br | " | |
| 110 | " | benzyl | H | " | |
| 111 | " | 4-chlorophenylthio | Cl | " | |
| 112 | " | 3-chloropropyl | " | " | |
| 113 | " | $C_2H_5$ | " | " | |
| 114 | " | 2-furyl | 2-furyl | " | 118–123 |
| 115 | " | 4-pyridyl | H | " | 138–142 |
| 116 | CN | 2-thienyl | Cl | $-N(CH_3)_2$ | |
| 117 | " | 4-fluoro-n-butyl | " | " | |
| 118 | " | 5-fluoropentyl | " | " | |
| 119 | " | n-$C_4H_9$ | " | " | |
| 120 | " | n-$C_5H_{11}$ | " | " | |
| 121 | " | n-$C_6H_{13}$ | " | " | |
| 122 | " | n-$C_7H_{15}$ | " | " | |
| 123 | " | n-$C_8H_{17}$ | " | " | |
| 124 | " | n-$C_{12}H_{25}$ | " | " | |
| 125 | " | iso-$C_3H_7$ | " | " | |
| 126 | " | iso-$C_4H_9$ | " | " | |
| 127 | " | tert-$C_4H_9$ | " | " | |
| 128 | " | cyclopropyl | " | " | |
| 129 | " | cyclohexyl | " | " | |
| 130 | " | $-CH_2CH=CH_2$ | " | " | |
| 131 | " | geranyl ($C_{10}H_{17}$) | " | " | |
| 132 | " | $SC_2H_5$ | " | " | |
| 133 | " | S-n-$C_3H_7$ | " | " | |
| 134 | " | S-n-$C_4H_9$ | " | " | 36–38 |

TABLE 2-continued (I)

structure: R1, SO2R4 on carbon bonded to N; R2, R3 on other carbon with N; double bond between

| Compound No. | R₁ | R₂ | R₃ | R₄ | Melting Point (°C.) |
|---|---|---|---|---|---|
| 135 | " | benzylthio | " | " | |
| 136 | " | 3-trifluoromethyl-2-pyridylthio | " | " | |
| 137 | " | " | H | " | |
| 138 | CN | 4-chlorophenylthio | H | —N(CH₃)₂ | |
| 139 | " | S-n-C₃H₇ | " | " | |
| 140 | " | SC₂H₅ | " | " | |
| 141 | " | phenylthio | phenylthio | " | 98–101 |
| 142 | " | " | C₂H₅ | " | |
| 143 | " | benzenesulfonyl | H | " | |
| 144 | " | 2-fluorobenzenesulfonyl | " | " | |
| 145 | " | 4-chlorobutyl | Cl | " | |
| 146 | " | 5-chloropentyl | " | " | |
| 147 | " | CH₂OCH₃ | " | " | |
| 148 | " | CH₂OC₂H₅ | " | " | |
| 149 | " | 1-hydroxypropyl | " | " | |
| 150 | " | 1-hydroxybutyl | " | " | |
| 151 | " | benzyl | " | " | 94–97 |
| 152 | " | 4-methylbenzyl | " | " | |
| 153 | " | 3-methylbenzyl | " | " | |
| 154 | " | 2-methylbenzyl | " | " | |
| 155 | " | 2-fluorobenzyl | " | " | |
| 156 | " | phenethyl | " | " | |
| 157 | " | n-C₃H₇ | Br | " | |
| 158 | " | n-C₄H₉ | " | " | |
| 159 | CN | n-C₅H₁₁ | Br | —N(CH₃)₂ | |
| 160 | " | n-C₆H₁₃ | " | " | |
| 161 | " | iso-C₃H₇ | " | " | |
| 162 | " | iso-C₄H₉ | " | " | |
| 163 | " | cyclopropyl | " | " | |
| 164 | " | cyclohexyl | " | " | |
| 165 | " | 4-chlorophenylthio | " | " | |
| 166 | " | OCH₂CF₃ | " | " | 77–79 |
| 167 | " | S-n-C₃H₇ | " | " | |
| 168 | " | S-n-C₄H₉ | " | " | |
| 169 | " | S-iso-C₄H₉ | " | " | |
| 170 | " | CH₂OCH₃ | " | " | |
| 171 | " | CH₂OC₂H₅ | " | " | |
| 172 | " | methoxycarbonyl | " | " | |
| 173 | " | N-(4-chlorophenyl)carbamoyl | " | " | |
| 174 | " | N-phenylcarbamoyl | " | " | |
| 175 | " | N-ethylcarbamoyl | " | " | |
| 176 | —CSNH₂ | C₂H₅ | Cl | " | |
| 177 | N-acetylthiocarbamoyl | " | " | " | |
| 178 | —CSNH₂ | n-C₄H₉ | " | " | |
| 179 | N-acetylthiocarbamoyl | n-C₄H₉ | Cl | —N(CH₃)₂ | |
| 180 | CN | H | I | " | 101–105 |
| 181 | " | n-C₃H₇ | " | " | |
| 182 | " | " | —COCF₃ | " | |
| 183 | —CSNH₂ | " | Br | " | |
| 184 | N-acetylthiocarbamoyl | " | " | " | |
| 185 | —CSNH₂ | " | Cl | " | |
| 186 | N-acetylthiocarbamoyl | " | " | " | |
| 187 | N-priopionylthiocarbamoyl | " | " | " | |
| 188 | N-methylthiocarbamoyl | phenyl | " | " | |
| 189 | N-acetylthiocarbamoyl | " | " | " | |
| 190 | CN | —SO₂N(CH₃)₂ | H | " | 142–149 |
| 191 | " | —Si(CH₃)₃ | Cl | " | |
| 192 | " | n-C₁₀H₂₁ | " | " | |
| 193 | " | C₂H₅ | H | " | |
| 194 | " | n-C₄H₉ | " | " | |
| 195 | " | S-n-C₄H₉ | " | " | |
| 196 | CN | 1-hydroxy-3-phenylpropyl | Cl | —N(CH₃)₂ | |
| 197 | " | 1-hydroxypropyl | H | " | |
| 198 | " | α-hydroxybenzyl | Cl | " | |
| 199 | " | α-acetoxybenzyl | " | " | |
| 200 | " | 1-hydroxy-3-methylbutyl | " | " | |
| 201 | " | 4-methyl-3-chlorophenyl | " | " | |
| 202 | " | " | Br | " | |
| 203 | " | 4-methoxy-3-chlorophenyl | Cl | " | |
| 204 | " | " | Br | " | |
| 205 | " | 2,3-dichlorophenyl | Cl | " | |
| 206 | " | 4-ethoxyphenyl | " | " | |
| 207 | " | " | Br | " | |
| 208 | " | 3,4-methylenedioxyphenyl | Cl | " | |

TABLE 2-continued $$\underset{SO_2R_4}{\overset{R_1}{\diagdown}}\underset{N}{\overset{N}{\diagup}}\underset{R_3}{\overset{R_2}{\diagdown}}\qquad(I)$$

| Compound No. | $R_1$ | $R_2$ | $R_3$ | $R_4$ | Melting Point (°C.) |
|---|---|---|---|---|---|
| 209 | " | " | Br | " | |
| 210 | " | 4-cyanophenyl | Cl | " | |
| 211 | " | " | Br | " | |
| 212 | " | 4-nitrophenyl | Cl | " | 140–145 |
| 213 | " | 2-butenyl | " | " | |
| 214 | " | iso-$C_5H_{11}$ | " | " | |
| 215 | —$CSNH_2$ | H | Cl | —$N(CH_3)_2$ | |
| 216 | " | $CH_3$ | " | " | |
| 217 | " | $C_5H_{11}$ | " | " | |
| 218 | " | benzyl | " | " | |
| 219 | N-acetylthiocarbamoyl | H | " | " | |
| 220 | " | $CH_3$ | " | " | |
| 221 | " | $C_5H_{11}$ | " | " | |
| 222 | " | benzyl | " | " | |
| 223 | N-propionylthiocabamoyl | " | " | " | |
| 224 | —$CSNH_2$ | $C_2H_5$ | Br | " | |
| 225 | N-acetylthiocarbamoyl | " | " | " | |
| 226 | N-propionylthiocarbamoyl | " | " | " | |
| 227 | CN | 3-chlorobutyl | Cl | " | |
| 228 | " | —$CF_2CF$=$CF_2$ | H | " | |
| 229 | " | sec-$C_4H_9$ | Cl | " | |
| 230 | " | —$CH_2CH$=$C(CH_3)_2$ | " | " | |
| 3-b | CN | n-$C_3H_7$ | H | —$N(CH_3)_2$ | 51–52 |
| 9-b | " | $SCH_3$ | " | " | 114–115 |
| 10-b | " | phenylthio | " | " | 106–107 |
| 14-b | " | H | Cl | " | 111–114 |
| 15-b | " | $CH_3$ | " | " | 90–95 |
| 16-b | " | n-$C_3H_7$ | " | " | 64–66 |
| 17-b | " | phenyl | " | " | 109–112 |
| 18-b | " | 4-methylphenyl | " | " | 133–134 |
| 19-b | " | 3-methylphenyl | " | " | |
| 20-b | " | 2-methylphenyl | " | " | 93–96 |
| 21-b | " | 3,4-dimethylphenyl | " | " | |
| 22-b | " | 4-methoxyphenyl | " | " | |
| 23-a | " | 4-chlorophenyl | " | " | 133–138 |
| 23-b | " | " | " | " | 117–120 |
| 24-b | " | 2-chlorophenyl | " | " | 113–117 |
| 25-b | " | 3,4-dichlorophenyl | " | " | |
| 26-b | " | 4-fluorophenyl | " | " | 120–122 |
| 27-b | " | $SCH_3$ | " | " | 101–103 |
| 28-b | " | phenylthio | " | " | 107–108 |
| 29-b | " | H | Br | " | 100–103 |
| 30-b | " | $CH_3$ | " | " | 107–110 |
| 31-b | " | tert-$C_4H_9$ | " | " | |
| 32-b | CN | phenyl | Br | —$N(CH_3)_2$ | 122–124 |
| 33-b | " | 4-methylphenyl | " | " | 136–137 |
| 34-b | " | 4-tert-butylphenyl | " | " | |
| 35-b | " | 4-methoxyphenyl | " | " | |
| 36-b | " | 4-fluorophenyl | " | " | |
| 37-b | " | 4-chlorophenyl | " | " | |
| 39-b | " | $C_2H_5$ | " | " | 112–115 |
| 40-b | " | —$CH_2CH$=$CH_2$ | " | " | 92–94 |
| 41-b | " | 4-bromophenyl | Cl | " | |
| 42-a | " | 4-isopropylphenyl | " | " | 110–114 |
| 42-b | " | " | " | " | 135–138 |
| 43-b | " | 2-naphthyl | " | " | |
| 46-b | " | phenyl | $SCH_3$ | " | 99–101 |
| 49-b | —$CSNH_2$ | " | H | " | |
| 50-b | " | 4-chlorophenyl | " | " | |
| 51-b | " | phenyl | Cl | " | 115–128 |
| 52-b | " | H | Br | " | |
| 53-b | " | phenyl | " | " | 110–118 |
| 55-b | CN | 3-methyl-4-methoxyphenyl | Cl | " | 115–118 |
| 56-b | " | 4-ethylphenyl | " | " | 110–112 |
| 57-b | " | phenylthio | Br | " | 94–97 |
| 58-b | CN | benzyl | Br | —$N(CH_3)_2$ | 87–89 |
| 59-b | " | 3-chloropropyl | H | " | |
| 60-b | " | —$SO_2C_2H_5$ | " | " | 121–124 |
| 61-b | " | 3-fluoropropyl | Cl | " | 75–79 |
| 65-b | " | 2-chlorophenyl | Br | " | 119–123 |
| 67-b | " | 4-(2',2',2'-trifluoroethoxy)phenyl | Cl | " | 111–113 |
| 68-b | " | " | Br | " | 115–118 |
| 69-b | " | —$CH_2OH$ | H | " | 106–107 |
| 70-b | " | 3-chlorophenyl | Cl | " | 96–99 |

TABLE 2-continued $$\underset{SO_2R_4}{\overset{R_1}{\diagdown}}\underset{N}{\overset{N}{\diagup}}\underset{R_3}{\overset{R_2}{\diagdown}} \quad (I)$$

| Compound No. | $R_1$ | $R_2$ | $R_3$ | $R_4$ | Melting Point (°C.) |
|---|---|---|---|---|---|
| 71-b | " | 3-fluorophenyl | " | " | |
| 72-b | " | 2-fluorophenyl | " | " | |
| 73-b | " | —SCH$_2$CH=CH$_2$ | H | " | 20–30 |
| 75-b | " | 1,2-diphenylethyl | " | " | 101–103 |
| 76-b | " | α-hydroxybenzyl | " | " | 98–100 |
| 103-b | " | phenyl | Cl | —N(C$_2$H$_5$)$_2$ | 99–101 |
| 104-b | " | " | Br | " | |
| 105-b | " | " | Cl | morpholino | |
| 106-b | " | " | Br | " | 126–130 |
| 111-b | " | 4-chlorophenylthio | Cl | —N(CH$_3$)$_2$ | 92–94 |
| 112-b | " | 3-chloropropyl | " | " | 102–105 |
| 113-b | " | C$_2$H$_5$ | " | " | 95–97 |
| 119-b | " | n-C$_4$H$_9$ | " | " | 48–49 |
| 120-b | CN | n-C$_5$H$_{11}$ | Cl | —N(CH$_3$)$_2$ | 37–39 |
| 121-b | " | n-C$_6$H$_{13}$ | " | " | $n_D^{23.5}$ 1.5002 |
| 122-b | " | n-C$_7$H$_{15}$ | " | " | $n_D^{23.5}$ 1.5019 |
| 123-b | " | n-C$_8$H$_{17}$ | " | " | $n_D^{23.6}$ 1.4981 |
| 124-b | " | n-C$_{12}$H$_{25}$ | " | " | 34–36 |
| 125-b | " | iso-C$_3$H$_7$ | " | " | 75–82 (decomposed) |
| 126-b | " | iso-C$_4$H$_9$ | " | " | 73–76 |
| 127-b | " | tert-C$_4$H$_9$ | " | " | 74–80 |
| 128-b | " | cyclopropyl | " | " | 76–79 |
| 129-b | " | cyclohexyl | " | " | 107–111 |
| 130-b | " | —CH$_2$CH=CH$_2$ | " | " | 67–72 |
| 131-b | " | geranyl (C$_{10}$H$_{17}$) | " | " | |
| 132-b | " | SC$_2$H$_5$ | " | " | 107–110 |
| 133-b | " | S-n-C$_3$H$_7$ | " | " | 70–74 |
| 134-b | " | S-n-C$_4$H$_9$ | " | " | |
| 135-b | " | benzylthio | " | " | 149–152 |
| 136-b | " | 3-trifluoromethyl-2-pyridylthio | " | " | 126–127 |
| 137-b | " | " | H | " | 109–111 |
| 138-b | " | 4-chlorophenylthio | " | " | 110–112 |
| 140-a | " | SC$_2$H$_5$ | " | " | 36–40 |
| 140-b | CN | SC$_2$H$_5$ | H | —N(CH$_3$)$_2$ | 41–45 |
| 142-a | " | phenylthio | C$_2$H$_5$ | " | 86–89 |
| 145-b | " | 4-chlorobutyl | Cl | " | $n_D^{22.1}$ 1.5382 |
| 146-b | " | 5-chloropentyl | " | " | $n_D^{24.8}$ 1.5328 |
| 147-b | " | CH$_2$OCH$_3$ | " | " | 64–66 |
| 148-b | " | CH$_2$OC$_2$H$_5$ | " | " | 82–84 |
| 149-b | " | 1-hydroxypropyl | " | " | 70–73 |
| 150-b | " | 1-hydroxybutyl | " | " | $n_D^{24.2}$ 1.5097 |
| 151-b | " | benzyl | " | " | 92–100 |
| 152-b | " | 4-methylbenzyl | " | " | 125–129 |
| 153-b | " | 3-methylbenzyl | " | " | 93–96 |
| 154-b | " | 2-methylbenzyl | " | " | 119–123 |
| 155-b | " | 2-fluorobenzyl | " | " | 105–109 |
| 156-b | " | phenethyl | " | " | 106–110 |
| 157-b | " | n-C$_3$H$_7$ | Br | " | 93–94 |
| 158-b | " | n-C$_4$H$_9$ | " | " | |
| 159-b | " | n-C$_5$H$_{11}$ | " | " | |
| 160-b | " | n-C$_6$H$_{13}$ | " | " | 99–101 |
| 161-b | " | iso-C$_3$H$_7$ | " | " | |
| 162-b | " | iso-C$_4$H$_9$ | " | " | |
| 163-b | " | cyclopropyl | " | " | |
| 164-b | " | cyclohexyl | " | " | |
| 165-b | CN | 4-chlorophenylthio | Br | —N(CH$_3$)$_2$ | 94–95 |
| 167-b | " | S-n-C$_3$H$_7$ | " | " | 76–78 |
| 168-b | " | S-n-C$_4$H$_9$ | " | " | 48–50 |
| 169-b | " | S-iso-C$_4$H$_9$ | " | " | 77–79 |
| 170-b | " | CH$_2$OCH$_3$ | " | " | 65–67 |
| 171-b | " | CH$_2$OC$_2$H$_5$ | " | " | 100–101 |
| 172-b | " | methoxycarbonyl | " | " | 98–101 |
| 173-b | " | N-(4-chlorophenyl)carbamoyl | " | " | 106–109 |
| 174-b | " | N-phenylcarbamoyl | " | " | 105–107 |
| 175-b | " | N-ethylcarbamoyl | " | " | 98–101 |
| 181-a | " | n-C$_3$H$_7$ | I | " | 76–79 |
| 181-b | " | " | " | " | 99–103 |
| 182-a | " | " | —COCF$_3$ | " | 90–92 |
| 185-b | —CSNH$_2$ | " | Cl | " | 160–162 |
| 186-b | N-acetylthiocarbamoyl | " | " | " | 119–123 |
| 187-b | N-propionylthiocarbamoyl | " | " | " | 150–152 |
| 188-b | N-methylthiocarbamoyl | phenyl | " | " | 67–72 |
| 189-b | N-acetylthiocarbamoyl | phenyl | Cl | —N(CH$_3$)$_2$ | 110–114 |

TABLE 2-continued $$\underset{SO_2R_4}{\overset{R_1}{\diagdown}}\underset{N}{\overset{N}{\diagup}}\underset{R_3}{\overset{R_2}{\diagdown}} \quad (I)$$

| Compound No. | R$_1$ | R$_2$ | R$_3$ | R$_4$ | Melting Point (°C.) |
|---|---|---|---|---|---|
| 191-b | CN | —Si(CH$_3$)$_3$ | " | " | 116–119 |
| 192-b | " | n-C$_{10}$H$_{21}$ | " | " | n$_D^{23.6}$ 1.4994 |
| 193-b | " | C$_2$H$_5$ | H | " | 69–71 |
| 194-b | " | n-C$_4$H$_9$ | " | " | 52–53 |
| 195-b | " | S-n-C$_4$H$_9$ | " | " | 50–51 |
| 196-b | " | 1-hydroxy-3-phenylpropyl | Cl | " | n$_D^{24.0}$ 1.5512 |
| 197-b | " | 1-hydroxypropyl | H | " | 94–97 |
| 198-b | " | α-hydroxybenzyl | Cl | " | 102–104 |
| 199-b | " | α-acetoxybenzyl | " | " | 82–86 |
| 200-b | " | 1-hydroxy-3-methylbutyl | " | " | 71–74 |
| 201-b | " | 4-methyl-3-chlorophenyl | " | " | 99–103 |
| 202-b | " | " | Br | " | 103–106 |
| 203-b | " | 4-methoxy-3-chlorophenyl | Cl | " | 97–101 |
| 204-b | " | " | Br | " | 105–110 |
| 205-b | " | 2,3-dichlorophenyl | Cl | " | 103–107 |
| 206-b | " | 4-ethoxyphenyl | " | " | 122–124 |
| 207-b | " | " | Br | " | 110–113 |
| 208-b | " | 3,4-methylenedioxyphenyl | Cl | " | 150–153 |
| 209-b | CN | 3,4-methylenedioxyphenyl | Br | —N(CH$_3$)$_2$ | 95–98 |
| 210-b | " | 4-cyanophenyl | Cl | " | 182–185 |
| 211-b | " | " | Br | " | 175–178 |
| 212-b | " | 4-nitrophenyl | Cl | " | 144–146 |
| 213-b | " | 2-butenyl | " | " | 87–90 |
| 214-b | " | iso-C$_5$H$_{11}$ | " | " | 45–47 |
| 218-b | —CSNH$_2$ | benzyl | " | " | 118–121 |
| 222-b | N-acetylthiocarbamoyl | " | " | " | 163–165 |
| 223-b | N-propionylthiocarbamoyl | " | " | " | 149–152 |
| 227-b | CN | 3-chlorobutyl | " | " | 54–57 |
| 230-b | " | —CH$_2$CH=C(CH$_3$)$_2$ | " | " | 75–78 |

Among the imidazole compounds of the present invention described in Table 2 above, the compounds having a mark "a" in their compound numbers are ones falling within the general formula (I-a) in the general formula (I) described hereinabove and the compounds having a mark "b" in their compound numbers are ones falling within the general formula (I-b) in the general formula (I) described hereinabove.

The imidazole compounds of the present invention are useful as biocides for controlling harmful organisms in the agricultural, horticultural, medical, and pharmaceutical areas.

As agricultural and horticultural fungicides, the compounds exhibit an excellent effect of controlling diseases of crop plants such as rice blast caused by *Pyricularia oryzae*, rice sheath blight caused by *Rhizoctonia solani*, oat crown rust caused by *Puccinia coronata*, cucumber anthracnose caused by *Colletotrichum lagenarium*, cucumber powdery mildew caused by *Sphaerotheca fuliginea*, cucumber downy mildew caused by *Pseudoperonospora cubensis*, tomato late blight caused by *Phytophthora infestans*, tomato early blight caused by *Alternaria solani*, citrus melanose caused by *Diaporthe citri*, citrus common green mold caused by *Penicillium digitatum*, pear scab caused by *Venturia nashicola*, apple alternaria blotch caused by *Alternaria mali*, grape downy mildew caused by *Plasmopara viticola*, and further gray mold caused by *Botrytis cinerea* and sclerotinia rot caused by *Sclerotinia sclerotiorum* of various crops, etc.; or soil diseases caused by phytopathogenic fungi such as Fusarium, Pythium, Rhizoctonia, Verticillium, Plasmodiophora, Aphanomyces, etc.

In particular, the compounds exhibit an excellent effect of preventing deseases such as potato or tomato late blight caused by *Phytophthora infestans*, cucumber downy mildew caused by *Pseudoperonospora cubensis*, grape downy mildew caused by *Plasmopara viticola*, and tobacco blue mold caused by *Peronospora tabacina*; and soil diseases caused by phycomycetes such as Plasmodiophora, Aphanomyces, Pythium, etc.

The compounds of the present invention have a prolonged residual effect so that they exhibit an excellent preventing effect, and further exhibit an excellent curative effect as well. Therefore, it is possible to control deseases by treatment after infection. The compounds of the present invention are appropriate to be applied to crop plants by foliar treatment. Further, the compounds possess a systemic activity so that it is also possible to control deseases of the stem and leaf by soil treatment. In addition, the compounds of the present invention show an excellent controlling effect against agriculturally and horticulturally harmful insects such as various planthoppers, diamondback moth (*Plutella xylostella*), green rice leafhopper (*Nephotettix cincticeps*), adzuki bean weevil (*Callosobruchus chinensis*), common cutworm (*Spodoptera litura*), green peach aphid (*Myzus persicae*), etc.; mites such as two-spotted spider mite (*Tetranychus urticae*), carmine spider mite (*Tetranychus cinnabarinus*), citrus red mite (*Panonychus citri*), etc.; and nematodes such as southern root-knot nematode (*Meloidogyne incognita*), etc.

Upon use, the compounds of the present invention can be prepared into a variety of forms of biocidal compositions such as emulsifiable concentrates, suspension concentrates, dusts, wettable powders, aqueous solutions, granules, etc., together with adjuvants, as in conventional formulations. Upon actual use of these formulations, they can be used as such or by diluting with a diluent such as water or the like to a predetermined concentration.

As the adjuvants used herein, mention may be made of carriers, emulsifying agents, suspending agents, dispersing agents, spreaders, penetrating agents, wetting agents, thickeners, stabilizers, etc.

The carriers are classified into solid carriers and liquid carriers. As the solid carriers, mention may be made of animal and vegetable powders such as starch, sugar, cellulose powders, cyclodextrin, activated charcoal, soybean powders, wheat powders, chaff powders, wood powders, fish powders, powdery milk, etc.; and mineral powders such as talc, kaolin, bentonite, bentonite-alkylamine complex, calcium carbonate, calcium sulfate, sodium bicarbonate, zeolite, diatomaceous earth, white carbon, clay, alumina, silica, sulfur powders, etc. As the liquid carriers, mention may be made of water; animal and vegetable oils such as corn oil, soybean oil, cotton seed oil, etc.; alcohols such as ethyl alcohol, ethylene glycol, etc.; ketones such as acetone, methyl ethyl ketone, etc.; ethers such as dioxane, tetrahydrofuran, etc.; aliphatic hydrocarbons such as kerosene, lamp oil, liquid paraffin, etc.; aromatic hydrocarbons such as xylene, trimethylbenzene, tetramethylbenzene, cyclohexane, solvent naphtha, etc.; halogenated hydrocarbons such as chloroform, chlorobenzene, etc.; acid amides such as dimethylformamide, etc.; esters such as ethyl acetate, fatty acid glycerine esters, etc.; nitriles such as acetonitrile, etc.; sulfur-containing compounds such as dimethyl sulfoxide, etc.; and N-methyl pyrrolidone, etc.

The adjuvants other than the carriers described hereinabove, such as emulsifying agents, suspending agents, dispersing agents, spreaders, penetrating agents, wetting agents, thickeners, stabilizers, etc. are exemplified more specifically as following surfactants.

Polyoxyethylene alkylarylether, polyoxyethylene glycol nonyl phenylether, polyoxyethylene laurylether, polyoxyethylene caster oil, polyoxyethylene alkylaryl sulfate (polyoxyethylene alkylphenyl ether sulfate), polyoxyethylene fatty acid ester (polyoxyethylene stearate), polyoxyethylene sorbitan fatty acid ester, lower alcohol phosphate, sodium alkylsulfate, sodium lignin sulfonate, calcium lignin sulfonate, alkylaryl sulfonate, sodium alkylbenzene sulfonate, sodium $\beta$-naphthalene sulfonate-formaldehyde condensate, dialkylsulfosuccinate.

The compound of the present invention is uniformly mixed with at least one kind of adjuvants described hereinabove to form a biocidal composition.

A weight ratio of the compound of the present invention to the adjuvants to be formulated is generally from 0.05:99.95 to 90:10, preferably from 0.2:99.8 to 80:20.

Since a concentration of the compound of the present invention to be applied may vary depending upon crop to be applied, method for application, preparation form, dose to be applied, etc., it is difficult to define a specific concentration range. However, if it is forced to define specifically, the concentration of the compound is generally from 0.1 to 10,000 ppm, desirably from 1 to 2,000 ppm in the case of foliar treatment, and is generally from 10 to 100,000 g/ha, desirably from 200 to 20,000 g/ha in the case of soil treatment.

Further, if necessary and desired, the compound of the present invention can be used as admixture with or in combination with other agricultural chemicals, for example, insecticides, acaricides, nematocides, fungicides, antiviral agents, attractants, herbicides, plant growth regulators, etc. In this case, more excellent effects can sometimes be exhibited.

As the insecticides, acaricides or nematocides, mention may be made of, for example, organic phosphrous compounds, carbamate compounds, organic chlorine compounds, organic metal compounds, pyrethroid compounds, benzoyl urea compounds, juvenile hormone-like compounds, dinitro compounds, organic sulfur compounds, urea compounds, triazine compounds, etc. The compound of the present invention can also be used as admixture with or in combination with biological pesticides such as BT agents, insect pathogenic viral agents, etc.

As the fungicides, mention may be made of, for example, organic phosphorus compounds, organic chlorine compounds, dithiocarbamate compounds, N-halogenothioalkyl compounds, dicarboximide compounds, benzimidazole compounds, azole compounds, carbinol compounds, benzanilide compounds, acylalanine compounds, pyridinamine compounds, piperazine compounds, morpholine compounds, anthraquinone compounds, quinoxaline compounds, crotonic acid compounds, sulfenic acid compounds, urea compounds, antibiotics, etc.

On the other hand, as medical and pharmaceutical antimicrobial agent, the compounds of the present invention are effective against microorganisms belonging to Staphylococcus and Trichophyton.

Upon use, the compounds can be orally and unorally administered similarly to the conventional medicines.

In the case of oral administating use, the compounds may be formulated into various types suited for gastroenteral absorption such as tablets, granules, capsules, syrup, aqueous or oily suspensions, and the like.

And, in the case of unoral administrating use, compounds may be formulated for injection or into various types suited for cuteneous absorption such as creams, ointments, and the like.

Preferable dose varies according to the conditions such as etat, age, etc. of human beings and animals infected with pathogen.

Hereafter, test examples of the biocidal compositions for controlling harmful organisms in the agricultural, horticulatural, medical, and pharamceutical areas in accordance with the present invention are described below.

Standards for evaluation of the agricultural and horticultural fungicides follow the following criteria for evaluation, unless otherwise indicated.

Standards for Evaluation

The controlling effect was determined by visually observing a degree of desease of a test plant and expressed by the following 5 grades of the index of control.

| [Index of Control] | [Degree of Desease] |
| --- | --- |
| 5: | No lesion is noted at all. |
| 4: | Area, number or length of lesions is less than 10% as compared to the non-treated plot. |
| 3: | Area, number or length of lesions is less than 40% as compared to the non-treated plot. |
| 2: | Area, number or length of lesions is less than 70% as compared to the non-treated plot. |
| 1: | Area, number or length of lesions is more than 70% as compared to the non- |

-continued

| [Index of Control] | [Degree of Desease] |
|---|---|
| | treated plot. |

TEST EXAMPLE 1

Test on preventive effect against cucumber powdery mildew

Cucumber (cultivars: Suyo) was cultivated in a polyethylene pot having a diameter of 7.5 cm. When cucumber reached the one-leaf stage, 10 ml of a solution obtained from each of test compounds adjusted to a predetermined concentration was sprayed over cucumber using a spray gun. After keeping the pots in a constant temperature chamber of 22° to 24° C. over one day and one night, conidia of fungi of powdery mildew (*Sphaerotheca fuliginea*) were inoculated. Ten days after the inoculation, an area of lesion on the first leaf was investigated, and an index of control was determined by the standards for evaluation described above. The results shown in Table 3 were obtained.

TABLE 3

| Compound No. | Index of Control 500 ppm |
|---|---|
| 15-b | 4 |
| 23-a | 4 |
| 59-b | 4 |
| 106-b | 3 |
| 133-b | 4 |
| 167-b | 3 |
| 169-b | 3 |
| 171-b | 5 |

TEST EXAMPLE 2

Test on preventive effect against cucumber anthracnose

Cucumber (cultivars: Suyo) was cultivated in a polyethylene pot having a diameter of 7.5 cm. When cucumber reached the two-leaf stage, 10 ml of a solution obtained from each of test compounds adjusted to a predetermined concentration was sprayed over cucumber using a spray gun. After keeping the pots in a constant temperature chamber of 22° to 24° C. over one day and one night, a spore suspension of fungi of anthracnose (*Colletotrichum lagenarium*) was inoculated. Seven days after the inoculation, an area of lesion on the first leaf was investigated, and an index of control was determined by the standards for evaluation described above. The results shown in Table 4 were obtained.

TABLE 4

| Compound No. | Index of Control 500 ppm |
|---|---|
| 3-b | 3 |
| 17-b | 3 |
| 26 | 5 |
| 28-b | 3 |
| 51 | 3 |
| 51-b | 3 |
| 59-b | 3 |
| 69-b | 3 |
| 70-b | 4 |
| 73-b | 3 |
| 75-b | 3 |
| 101 | 4 |
| 105 | 4 |
| 106 | 3 |

TEST EXAMPLE 3

Test on preventive effect against cucumber downy mildew

Cucumber (cultivars: Suyo) was cultivated in a polyethylene pot having a diameter of 7.5 cm. When cucumber reached the two-leaf stage, 10 ml of a solution obtained from each of test compounds adjusted to a predetermined concentration was sprayed over cucumber using a spray gun. After keeping the pots in a constant temperature chamber of 22° to 24° C. over one day and one night, a spore suspension of fungi of downy mildew (*Pseudoperonospora cubensis*) was inoculated. Six days after the inoculation, an area of lesion on the first leaf was investigated, and an index of control was determined by the standards for evaluation described above. The results shown in Table 5 were obtained.

TABLE 5

| Compound No. | Index of Control | | Compound No. | Index of Control | |
|---|---|---|---|---|---|
| | 125 ppm | 31 ppm | | 125 ppm | 31 ppm |
| 4 | 5 | 5 | 29-b | 5 | 5 |
| 5 | 5 | 5 | 30-b | 5 | 5 |
| 6 | 5 | 4 | 31 | 4 | 3 |
| 7 | 5 | 5 | 32-b | 5 | 5 |
| 8 | 5 | 3 | 33 | — | 5 |
| 14-b | 5 | 3 | 34 | 5 | 5 |
| 15-b | 5 | 5 | 36 | — | 5 |
| 16-b | — | 5 | 37 | 5 | 5 |
| 17 | 5 | 5 | 45 | 5 | 5 |
| 17-b | — | 5 | 47 | 5 | 5 |
| 23 | 5 | 5 | 48 | 5 | 5 |
| 49 | 5 | 4 | 101 | 5 | 4 |
| 50 | 5 | 5 | 103 | 5 | 5 |
| 52 | 5 | 5 | 105 | 4 | — |
| 53-b | 5 | 5 | 106 | 5 | 5 |

TEST EXAMPLE 4

Test on curative effect against cucumber downy mildew

Cucumber (cultivars: Suyo) was cultivated in a polyethylene pot having a diameter of 7.5 cm. When cucumber reached the two-leaf stage, a spore suspension of fungi of downy mildew (*Pseudoperonospora cubensis*) was inoculated. Six ours after the inoculation, 10 ml of a solution obtained from each of test compounds adjusted to a predetermined concentration was sprayed over cucumber using a spray gun. After keeping the pots in a constant temperature chamber of 22° to 24° C. for 6 days, an area of lesion on the first leaf was investigated, and an index of control was determined by the standards for evaluation described above. The results shown in Table 6 were obtained.

TABLE 6

| Compound No. | Index of Control | | Compound No. | Index of Control | |
|---|---|---|---|---|---|
| | 125 ppm | 31 ppm | | 125 ppm | 31 ppm |
| 3-b | 5 | — | 8 | 5 | — |
| 9-b | 5 | — | 32-b | 5 | — |
| 10-b | 5 | — | 33 | 5 | — |
| 12 | 5 | — | 33-b | 5 | — |
| 14-b | 5 | — | 36 | 5 | — |
| 15-b | 5 | — | 37 | 5 | — |
| 16-b | 5 | — | 39-b | — | 5 |
| 17 | 5 | — | 40-b | — | 5 |
| 17-b | 5 | — | 41 | — | 5 |
| 18 | — | 5 | 46-a | 5 | — |
| 18-b | 5 | — | 48 | 4 | — |
| 19 | 5 | — | 51 | 5 | — |
| 20-b | 5 | — | 51-b | 5 | — |
| 22 | 5 | — | 52 | 5 | — |

TABLE 6-continued

| Compound No. | Index of Control 125 ppm | 31 ppm | Compound No. | Index of Control 125 ppm | 31 ppm |
|---|---|---|---|---|---|
| 23 | 5 | — | 53-b | 5 | — |
| 23-a | 5 | — | 56-b | 5 | — |
| 23-b | 5 | — | 57-b | — | 5 |
| 24-b | — | 5 | 58-b | — | 5 |
| 25 | — | 4 | 59-b | — | 5 |
| 26 | — | 5 | 60-b | — | 5 |
| 26-b | 5 | — | 61-b | — | 5 |
| 27-b | 5 | — | 65-b | 5 | — |
| 28-b | 5 | — | 67-b | 5 | — |
| 29-b | 5 | — | 68-b | — | 4 |
| 30-b | 5 | — | 69-b | 4 | — |
| 70-b | 5 | — | 138-b | — | 5 |
| 72 | — | 5 | 141 | 4 | — |
| 74 | — | 4 | 142-a | 5 | 5 |
| 76-b | 5 | — | 145-b | — | 5 |
| 88 | — | 5 | 146-b | — | 5 |
| 101 | 4 | — | 147-b | 5 | 5 |
| 103-b | 5 | — | 148-b | 5 | 5 |
| 106-b | 5 | — | 149-b | — | 5 |
| 111-b | — | 5 | 150-b | 5 | — |
| 112-b | 5 | 5 | 151 | — | 5 |
| 113-b | 5 | 5 | 151-b | 5 | 5 |
| 119-b | 5 | 5 | 152-b | — | 3 |
| 120-b | 5 | 5 | 153-b | — | 5 |
| 121-b | 5 | 5 | 154-b | — | 5 |
| 125-b | — | 5 | 155-b | — | 5 |
| 126-b | — | 5 | 156-b | — | 5 |
| 128-b | — | 5 | 157-b | — | 5 |
| 129-b | — | 5 | 160-b | 5 | 5 |
| 130-b | 5 | 5 | 166 | 5 | 3 |
| 132-b | — | 5 | 167-b | 5 | 5 |
| 133-b | 5 | 4 | 169-b | 5 | 5 |
| 134 | 5 | 5 | 170-b | 5 | 5 |
| 135-b | 4 | — | 171-b | 5 | 5 |
| 136-b | — | 3 | 173-b | 4 | — |
| 180 | 5 | — | 201-b | 4 | — |
| 181-a | — | 5 | 203-b | 3 | — |
| 181-b | — | 5 | 208-b | 4 | 3 |
| 185-b | — | 5 | 209-b | 5 | — |
| 186-b | — | 5 | 210-b | 4 | — |
| 187-b | — | 5 | 212-b | 5 | 5 |
| 189-b | 5 | 5 | 213-b | — | 5 |
| 190 | 5 | 4 | 214-b | — | 5 |

TEST EXAMPLE 5

Test on systemic effect against cucumber downy mildew

Cucumber (cultivars: Suyo) was cultivated in a polyethylene pot having a diameter of 7.5 cm. When cucumber reached the two-leaf stage, 15 ml of a solution obtained from each of test compounds adjusted to a predetermined concentration was drenched on the surface of soil using a pipette. After keeping the pots in a constant temperature chamber of 22° to 24° C. for 2 days, a spore suspension of fungi of downy mildew (*Pseudoperonospora cubensis*) was inoculated. Six days after the inoculation, an area of lesion on the first leaf was investigated, and an index of control was determined by the standards for evaluation described above. The results shown in Table 7 were obtained.

TABLE 7

| Compound No. | Index of Control 500 pm | 125 ppm |
|---|---|---|
| 1 | 5 | 3 |
| 14-b | 5 | 5 |
| 15-b | — | 5 |
| 17 | 5 | 4 |
| 29-b | 5 | 5 |
| 30-b | 5 | 5 |
| 37 | 5 | 5 |
| 52 | 5 | 5 |

TABLE 7-continued

| Compound No. | Index of Control 500 pm | 125 ppm |
|---|---|---|
| 53-b | 5 | 5 |

TEST EXAMPLE 6

Test on preventive effect against tomato late blight

Tomato (cultivars: Ponderosa) was cultivated in a polyethylene pot having a diameter of 7.5 cm. When tomato reached the four-leaf stage, 10 ml of a solution obtained from each of test compounds adjusted to a predetermined concentration was sprayed over tomato using a spray gun. After keeping the pots in a constant temperature chamber of 22° to 24° C. over one day and one night, a zoosporangium suspension of fungi of late blight (*Phytophthora infestans*) was inoculated. Five days after the inoculation, an area of lesion on the leaves was investigated, and an index of control was determined by the standards for evaluation described above. The results shown in Table 8 were obtained.

TABLE 8

| Compound No. | Index of Control 125 ppm | 31 ppm | 8 ppm |
|---|---|---|---|
| 3-b | — | 5 | — |
| 4 | 5 | 4 | — |
| 5 | 5 | 5 | — |
| 6 | 5 | 4 | — |
| 7 | 5 | 5 | — |
| 8 | 5 | 5 | — |
| 9-b | — | 5 | — |
| 10-b | — | — | 5 |
| 12 | — | 5 | 3 |
| 14-b | — | 5 | — |
| 15-b | — | 4 | — |
| 16-b | — | 5 | 4 |
| 17 | 5 | 5 | — |
| 17-b | 5 | 5 | — |
| 18 | — | 5 | — |
| 18-b | — | 5 | — |
| 19 | — | 5 | — |
| 20-b | — | 5 | — |
| 21 | — | 5 | — |
| 22 | — | 5 | — |
| 23 | 5 | 5 | — |
| 23-a | — | 5 | — |
| 23-b | — | 5 | — |
| 24-b | — | 5 | 5 |
| 25 | — | 5 | 5 |
| 26 | — | 5 | — |
| 26-b | — | 5 | — |
| 27-b | — | 5 | — |
| 28-b | — | 5 | — |
| 29-b | 5 | 5 | — |
| 30-b | — | 5 | — |
| 32-b | 5 | 5 | — |
| 33 | 5 | 5 | — |
| 33-b | — | 5 | — |
| 34 | 4 | 4 | — |
| 36 | 5 | 5 | — |
| 37 | — | 5 | — |
| 39-b | — | — | 5 |
| 40-b | — | 5 | 5 |
| 41 | — | 5 | 5 |
| 42-a | — | 5 | — |
| 42-b | — | 5 | — |
| 43 | — | — | 5 |
| 45 | 5 | 5 | — |
| 46-a | 5 | 5 | — |
| 48 | 5 | 5 | — |
| 49 | 5 | 3 | — |
| 50 | 4 | — | — |
| 51 | 5 | 5 | — |
| 51-b | 5 | 5 | — |
| 52 | 5 | 4 | — |

TABLE 8-continued

| Compound No. | Index of Control | | |
|---|---|---|---|
| | 125 ppm | 31 ppm | 8 ppm |
| 53-b | 5 | 5 | — |
| 55-b | — | 4 | 5 |
| 56-b | — | 5 | — |
| 57-b | — | — | 5 |
| 58-b | — | 5 | 5 |
| 59-b | — | — | 5 |
| 60-b | — | 5 | — |
| 61-b | — | 5 | 5 |
| 65-b | — | 5 | — |
| 66 | 5 | 5 | — |
| 67-b | — | — | 5 |
| 68-b | — | — | 5 |
| 70-b | — | — | 5 |
| 72 | — | — | 5 |
| 73-b | — | 4 | — |
| 74 | — | — | 5 |
| 75-b | — | 5 | — |
| 76-b | — | 5 | — |
| 84 | — | — | 5 |
| 88 | — | — | 5 |
| 101 | 5 | 5 | — |
| 103 | 5 | — | — |
| 104 | 5 | 4 | — |
| 105 | 5 | 4 | — |
| 106-b | 5 | 4 | — |
| 111-b | — | — | 4 |
| 112-b | — | 5 | 5 |
| 113-b | — | — | 5 |
| 114 | — | 5 | 5 |
| 119-b | — | 5 | 5 |
| 120-b | — | 5 | 5 |
| 121-b | — | 5 | 5 |
| 122-b | — | 5 | 5 |
| 123-b | — | 5 | 5 |
| 124-b | — | 5 | 5 |
| 125-b | — | — | 5 |
| 126-b | — | — | 5 |
| 128-b | — | 5 | 4 |
| 129-b | — | 5 | 5 |
| 130-b | — | 5 | 5 |
| 132-b | — | 5 | — |
| 133-b | — | — | 5 |
| 134 | — | 5 | 5 |
| 135-b | — | 5 | 5 |
| 136-b | — | — | 5 |
| 137-b | — | — | 5 |
| 138-b | — | — | 4 |
| 141 | — | 5 | 5 |
| 142-a | — | 5 | 5 |
| 145-b | — | — | 4 |
| 146-b | — | 5 | 5 |
| 147-b | — | 4 | 3 |
| 148-b | — | 4 | — |
| 149-b | — | — | 5 |
| 151 | — | — | 5 |
| 151-b | — | 5 | 5 |
| 152-b | — | — | 5 |
| 153-b | — | — | 5 |
| 154-b | — | — | 5 |
| 155-b | — | — | 5 |
| 156-b | — | — | 5 |
| 157-b | — | — | 5 |
| 160-b | — | 5 | 5 |
| 166 | — | 5 | 3 |
| 167-b | — | 5 | 5 |
| 169-b | — | 5 | 5 |
| 170-b | — | 5 | 3 |
| 171-b | — | 5 | — |
| 173-b | — | 4 | 3 |
| 174-b | — | 4 | — |
| 180 | — | — | 5 |
| 181-b | — | 5 | 5 |
| 182-b | — | 5 | 5 |
| 185-b | — | — | 5 |
| 186-b | — | — | 5 |
| 187-b | — | 5 | 5 |
| 189-b | — | 5 | 4 |
| 190 | — | 4 | — |
| 201-b | — | 5 | 5 |
| 202-b | — | 5 | 5 |
| 203-b | — | 4 | 5 |
| 205-b | — | — | 5 |
| 206-b | — | 5 | 5 |
| 207-b | — | 5 | — |
| 208-b | — | 5 | 5 |
| 209-b | — | 4 | — |
| 210-b | — | 4 | 3 |
| 211-b | — | 4 | — |
| 212-b | — | 5 | 3 |
| 213-b | — | 5 | 5 |
| 214-b | — | 5 | 5 |

TEST EXAMPLE 7

Test on systemic effect against tomato late blight

Tomato (cultivars: Ponderosa) was cultivated in a polyethylene pot having a diameter of 7.5 cm. When tomato reached the four-leaf stage, 15 ml of a solution obtained from each of test compounds adjusted to a predetermined concentration was drenched on the surface of soil using a pipette. After keeping the pots in a constant temperature chamber of 22° to 24° C. for 2 days, a zoosporangium suspension of fungi of late blight (*Phytophthora infestans*) was inoculated. Five days after the inoculation, an area of lesion on the leaves was investigated, and an index of control was determined by the standards for evaluation described above. The results shown in Table 9 were obtained.

TABLE 9

| Compound No. | Index of Control | |
|---|---|---|
| | 500 ppm | 125 ppm |
| 3-b | — | 4 |
| 10-b | 5 | 5 |
| 16-b | — | 4 |
| 17-b | 5 | 4 |
| 19 | 4 | 4 |
| 20-b | 5 | 4 |
| 22 | 5 | 4 |
| 27-b | 5 | 5 |
| 28-b | 5 | — |
| 40-b | 5 | 5 |
| 51 | 5 | 5 |
| 51-b | 5 | 5 |
| 57-b | — | 4 |
| 58-b | 5 | 3 |
| 59-b | — | 4 |
| 76-b | — | 5 |

TEST EXAMPLE 8

Test on preventive effect against rice blast

Rice plant (cultivars: Chukyo Asahi) was cultivated in a polyethylene pot having a diameter of 7.5 cm. When rice plant reached the four-leaf stage, 20 ml of a solution obtained from each of test compounds adjusted to a predetermined concentration was sprayed over rice plant using a spray gun. After keeping the pots in a constant temperature chamber of 22° to 24° C. over one day and one night, a spore suspension of fungi of blast (*Pyricularia oryzae*) was inoculated. Five days after the inoculation, a number of lesion was investigated, and an index of control was determined by the standards for evaluation described above. The results shown in Table 10 were obtained.

TABLE 10

| Compound No. | Index of Control 500 ppm |
| --- | --- |
| 27-b | 4 |
| 48 | 3 |
| 53-b | 3 |
| 55-b | 4 |
| 134 | 3 |
| 167-b | 3 |
| 201-b | 4 |
| 202-b | 4 |

TEST EXAMPLE 9

Test on preventive effect against rice sheath blight

Rice plant (cultivars: Chukyo Asahi) was cultivated in a polyethylene pot having a diameter of 7.5 cm. When rice plant reached the five-leaf stage, 20 ml of a solution obtained from each of test compounds adjusted to a predetermined concentration was sprayed over rice plant using a spray gun. After keeping the pots in a constant temperature chamber of 22° to 24° C. over one day and one night, rice straw in which fungi of sheath blight (Rhizoctonia solani) had been previously incubated was set between leaf sheath portions to inoculate. After keeping the pots in an inoculation room having a temperature of 28° C. and a humidity of 100% for 5 days, a length of lesion was investigated, and an index of control was determined by the standards for evaluation described above. The results shown in Table 11 were obtained.

TABLE 11

| Compound No. | Index of Control 500 ppm |
| --- | --- |
| 6 | 3 |
| 21 | 3 |
| 27-b | 3 |
| 34 | 3 |
| 51-b | 3 |
| 53-b | 3 |
| 104 | 3 |

TEST EXAMPLE 10

Test on preventive effect against oat crown rust

Oats (cultivars: Zenshin) were cultivated in a polyethylene pot having a diameter of 7.5 cm. When oats reached the two-leaf stage, 10 ml of a solution obtained from each of test compounds adjusted to a predetermined concentration was sprayed over oats using a spray gun. After keeping the pots in a constant temperature chamber of 22° to 24° C. over one day and one night, conidia of fungi of crown rust (Puccinia coronata) were inoculated. Ten days after the inoculation, an area of lesion on the second leaf was investigated, and an index of control was determined by the standards for evaluation described above. The results shown in Table 12 were obtained.

TABLE 12

| Compound No. | Index of Control 500 ppm |
| --- | --- |
| 4 | 3 |
| 14-b | 3 |
| 44 | 4 |
| 52 | 4 |
| 59-b | 3 |
| 104 | 4 |
| 172-b | 4 |

TABLE 12-continued

| Compound No. | Index of Control 500 ppm |
| --- | --- |
| 180 | 5 |
| 190 | 3 |

TEST EXAMPLE 11

Test on preventive effect against turnip clubroot

Soil contaminated with fungi of clubroot (Plasmodiophora brassicae) was filled in a 1/14,000 a (1/140 m$^2$) pot, and 20 ml of a solution obtained from each of test compounds adjusted to 4 kg/10 a and 1 kg/10 a calculated as the active ingredient was drenched on the surface of the soil using a pipette. One day after treatment, the soil was mixed over the whole layers, and turnip (cultivars: Kanamachi Kokabu) was seeded. The turnip was grown in a greenhouse. Thirty days after the seeding, a degree of clubroot formation was investigated, and an index of control was determined by the standards for evaluation described below. The results shown in Table 13 were obtained.

Standards for Evaluation

| [Index of Control] | [Degree of Occurrence of Clubroot] |
| --- | --- |
| 5 | formation of clubroot none |
| 4 | formation of clubroot slight |
| 3 | formation of clubroot medium |
| 2 | formation of clubroot many |
| 1 | formation of clubroot abundant |

TABLE 13

| Compound No. | Index of Control 4 kg/10 a | 1 kg/10 a |
| --- | --- | --- |
| 1 | 5 | — |
| 4 | 4 | — |
| 5 | 5 | 5 |
| 6 | 5 | 5 |
| 7 | 5 | 5 |
| 8 | 5 | 5 |
| 9-b | 5 | 4 |
| 10-b | — | 5 |
| 12 | — | 5 |
| 14-b | 5 | 5 |
| 15-b | — | 5 |
| 16-b | 5 | 5 |
| 17 | — | 5 |
| 17-b | — | 5 |
| 18 | 5 | 5 |
| 18-b | — | 5 |
| 19 | 5 | 5 |
| 20-b | 5 | 4 |
| 21 | 5 | 5 |
| 22 | 5 | 5 |
| 23 | 5 | 5 |
| 23-a | — | 4 |
| 23-b | — | 4 |
| 24-b | — | 5 |
| 26 | 5 | 4 |
| 26-b | — | 5 |
| 27-b | 5 | 5 |
| 29-b | — | 5 |
| 30-b | — | 5 |
| 32-b | — | 5 |
| 33 | 5 | 5 |
| 33-b | — | 5 |
| 34 | 5 | 5 |
| 36 | 5 | 5 |
| 37 | 5 | 5 |
| 39-b | — | 5 |
| 40-b | — | 5 |
| 42-a | — | 5 |

TABLE 13-continued

| Compound No. | Index of Control | |
|---|---|---|
| | 4 kg/10 a | 1 kg/10 a |
| 42-b | — | 5 |
| 46-a | 5 | — |
| 49 | — | 4 |
| 50 | 5 | 5 |
| 51 | 5 | 5 |
| 51-b | 5 | 5 |
| 52 | — | 5 |
| 53-b | 5 | 4 |
| 55-b | — | 5 |
| 56-b | — | 5 |
| 58-b | — | 5 |
| 59-b | 5 | 5 |
| 65-b | — | 5 |
| 67-b | — | 5 |
| 68-b | — | 5 |
| 73-b | 4 | — |
| 88 | — | 4 |
| 105 | 4 | — |
| 106 | 5 | — |
| 180 | 5 | 5 |
| 201-b | — | 5 |
| 202-b | — | 5 |
| 206-b | — | 5 |
| 207-b | — | 5 |

TEST EXAMPLE 12

Antimicrobial test (phytopathogenic fungi)

Mycelial disc (agar punching) of preincubated *Pythium aphanidermatum* was transplanted on potato-dextrose agar medium (PDA medium) containing 100 ppm of streptomycin and 100 ppm of each of test compounds. After incubation at 22° C. for 48 hours, a diameter of mycelium was measured. Inhibition of hyphal growth (%) was determined by the following equation. The results shown in Table 14 were obtained.

inhibition of hyphal growth (%) =

$$100 - \frac{\text{Diameter of mycelium in treated plot}}{\text{Diameter of mycelium in non-treated plot}} \times 100$$

TABLE 14

| Compound No. | Inhibition of Hyphal Growth (%) |
|---|---|
| 3-b | 100 |
| 5 | 95 |
| 7 | 100 |
| 9-b | 100 |
| 10-b | 100 |
| 14-b | 100 |
| 15-b | 100 |
| 16-b | 100 |
| 17 | 100 |
| 17-b | 100 |
| 23 | 100 |
| 27-b | 100 |
| 28-b | 100 |
| 29-b | 100 |
| 30-b | 100 |
| 31 | 100 |
| 33 | 100 |
| 34 | 100 |
| 36 | 100 |
| 37 | 100 |
| 45 | 100 |
| 49 | 100 |
| 53-b | 100 |
| 101 | 100 |
| 103 | 100 |
| 104 | 100 |
| 105 | 100 |
| 106 | 100 |
| 180 | 100 |

TEST EXAMPLE 13

Miticidal test on adults of two-spotted spider mites

Kidney bean (cultivars: Edogawa Saito) was cultivated in a polyethylene pot having a diameter of 7.5 cm. When kidney bean reached the primary leaf stage, one primary leaf was left, and other leaves were cut out. After infesting about 30 adults of two-spotted spider mite (*Tetranychus urticae*: resistant to Dicofol and organic phosphorus insecticides), the seedlings were immersed in 20 ml of a solution obtained from each of test compounds adjusted to a predetermined concentration for about 10 seconds. After drying, the seedlings were allowed to stand in a constant temperature chamber of 26° C. with lighting. Two days after releasing the mites, numbers of dead mites were investigated, and a mortality (%) was determined by the following equation. The results shown in Table 15 were obtained.

$$\text{Mortality (\%)} = \frac{\text{Number of dead mites}}{\text{Number of released mites}} \times 100$$

TABLE 15

| Compound No. | Mortality (%) | |
|---|---|---|
| | 800 ppm | 200 ppm |
| 9-b | 100 | 100 |
| 10-b | 100 | 100 |
| 14-b | 100 | 100 |
| 15-b | 100 | 100 |
| 23 | 100 | 100 |
| 23-a | 100 | — |
| 23-b | 91 | — |
| 26-b | 100 | — |
| 29-b | 100 | 100 |
| 36 | 100 | 100 |
| 40-b | 100 | 100 |
| 41 | 100 | — |
| 52 | 100 | 100 |
| 57-b | 100 | — |
| 58-b | 100 | — |
| 72 | 100 | — |
| 88 | 100 | — |
| 101 | 100 | 100 |
| 112-b | 100 | — |
| 113-b | 100 | 100 |
| 119-b | 100 | 100 |
| 133-b | 100 | 90 |
| 151-b | 100 | — |
| 167-b | 100 | 87 |
| 169-b | 100 | 100 |
| 172-b | 100 | — |
| 205-b | 100 | — |

TEST EXAMPLE 14

Ovicidal test on two-spotted spider mites

Kidney bean with only one primary leaf was transplanted on a polyethylene pot. After infesting adults of two-spotted spider mite (*Tetranychus urticae*) and ovipositing for 24 hours, the adults were removed. Then, the kidney bean described above was immersed in 20 ml of a solution obtained from each of test compounds adjusted to a predetermined concentration for about 10 seconds. After drying, the kidney bean was kept in a constant temperature chamber of 26° C. with lighting. Five to seven days after the treatment, a state of hatching was investigated, and an ovicidal rate (%) was determined by the following equation. The results shown in Table 16 were obtained. Death immediately after hatching was regarded to be ovicidal.

$$\text{Ovicidal Rate (\%)} = \frac{\text{Number of killed eggs}}{\text{Number of oviposited eggs}} \times 100$$

TABLE 16

| Compound No. | Ovicidal Rate (%) 800 ppm |
|---|---|
| 10-b | 100 |
| 15-b | 100 |
| 26-b | 100 |
| 29-b | 100 |
| 30-b | 70 |
| 40-b | 100 |
| 52 | 98 |
| 57-b | 90 |
| 88 | 100 |
| 101 | 100 |
| 113-b | 100 |
| 119-b | 100 |
| 133-b | 100 |
| 167-b | 100 |
| 169-b | 100 |

TEST EXAMPLE 15

Insecticidal test on small brown planthoppers

Young seedlings of rice plant were immersed in 20 ml of a solution obtained from each of test compounds adjusted to a predetermined concentration for about 10 seconds. After drying, the root was wrapped with wet absorbent cotton and put in a test tube. Then, 10 larvae of second to third instar of small brown planthoppers (*Laodelphax striatellus*) were released in the test tube, and the opening of the test tube was covered with gauze. The test tube was kept in a constant temperature chamber of 26° C. with lighting. Five days after the release of the larvae, numbers of dead insects were investigated, and a mortality rate (%) was determined by the following equation. The results shown in Table 17 were obtained.

$$\text{Mortality (\%)} = \frac{\text{Number of dead insects}}{\text{Number of released insects}} \times 100$$

TABLE 17

| Compound No. | Mortality (%) 800 ppm | 200 ppm |
|---|---|---|
| 14-b | 100 | 100 |
| 15-b | 100 | 80 |
| 40-b | 100 | — |
| 113-b | 100 | — |
| 119-b | 100 | — |
| 133-b | 100 | — |
| 151-b | 100 | — |

TEST EXAMPLE 16

Insecticidal test on green peach aphids

A piece of cabbage leaf was immersed in 20 ml of a solution obtained from each of test compounds adjusted to a predetermined concentration for about 10 seconds, followed by drying. Wet filter paper was put on a petri dish having a diameter of 9 cm, and the air-dried leaf piece was put thereon. Apterous viviparous females of green peach aphids (*Myzus persicae*) were released on the leaf. The petri dish was covered and kept in a constant temperature chamber of 26° C. with lighting. Two days after release of the insects, numbers of dead insects were investigated, and a mortality (%) was determined in the same manner as Test Example 15 described above. The results shown in Table 18 were obtained.

TABLE 18

| Compound No. | Mortality (%) 800 ppm |
|---|---|
| 1 | 70 |
| 32-b | 70 |
| 52 | 90 |

TEST EXAMPLE 17

Insecticidal test on common cutworms

A piece of cabbage leaf was immersed in 20 ml of a solution obtained from each of test compounds adjusted to a predetermined concentration for about 10 seconds followed by drying. Wet filter paper was put on a petri dish having a diameter of 9 cm, and the air-dried leaf piece was put thereon. Second to third instar larvae of common cutworms (*Spodoptera litura*) were released on the leaf. The petri dish was covered and kept in a constant temperature chamber of 26° C. with lighting. Five days after release of the larvae, numbers of dead insects were investigated, and a mortality (%) was determined in the same manner as Test Example 15 described above. The results shown in Table 19 were obtained.

TABLE 19

| Compound No. | Mortality (%) 800 ppm |
|---|---|
| 26-b | 100 |
| 40-b | 100 |
| 67-b | 100 |
| 68-b | 100 |
| 72 | 100 |
| 74 | 100 |

TEST EXAMPLE 18

Antimicrobial test (fungi)

*Trichophyton metagrophytes* and *Trichophyton rubrum* were inoculated on Sabouraud agar medium containing 10 ppm of kanamycin and each of test compounds. After incubation at 28° to 30° C. for 5 days, growth of text fungi was examined. As the results, Compound Nos. 25, 34, 55-b, 119-b, and 168-b were effective against *Trichophyton metagrophytes*, and Compound No. 23 was effective against *Trichophyton rubrum*. Compound Nos. 26, 120-b, 134, and 169-b were effective against both fungi.

TEST EXAMPLE 19

Antimicrobial test (bacteria)

*Staphylococcus aureus* was inoculated on bouillon agar medium containing 10 ppm of each of test compounds. After incubation at 37° C. for 16 hours, growth of test bacteria was examined. As the results, Compound Nos. 17, 20-b, 21, 22, 23, 25, 26, 26-b, 28-b, 33, 34, 37, 41, 42-a, 43, 57-b, 67-b, 103, 104, 105, 106, 134, 168-b, 201-b, 202-b, 203-b, and 205-b were effective.

Formulation examples of the present invention are described below, but the compounds, dose in formulations, type of formulations, etc. in the present invention are not deemed to be limited to those described below.

FORMULATION EXAMPLE 1

Wettable powder

| | | |
|---|---|---|
| (a) Compound No. 5 | 50 | parts by weight |
| (b) Kaolin | 40 | parts by weight |
| (c) Sodium lignin sulfonate | 7 | parts by weight |
| (d) Dialkylsulfosuccinate | 3 | parts by weight |

The above components are uniformly mixed.

FORMULATION EXAMPLE 2

Wettable powder

| | | |
|---|---|---|
| (a) Compound No. 17-b | 20 | parts by weight |
| (b) Kaolin | 72 | parts by weight |
| (c) Sodium lignin sulfonate | 4 | parts by weight |
| (d) Polyoxyethylene alkylaryl ether | 4 | parts by weight |

The above components are uniformly mixed.

FORMULATION EXAMPLE 3

Wettable powder

| | | |
|---|---|---|
| (a) Compound No. 18-b | 6 | parts by weight |
| (b) Diatomaceous earth | 88 | parts by weight |
| (c) Dialkylsulfosuccinate | 2 | parts by weight |
| (d) Polyoxyethylene alkylaryl sulfate | 4 | parts by weight |

The above components are uniformly mixed.

FORMULATION EXAMPLE 4

Wettable Powder

| | | |
|---|---|---|
| (a) Kaolin | 78 | parts by weight |
| (b) Sodium β-naphthalene-sulfonate-formaldehyde condensate | 2 | parts by weight |
| (c) Polyoxyethylene alkylaryl sulfate | 5 | parts by weight |
| (d) Fine silica | 15 | parts by weight |

A mixture of the above components and Compound No. 22 are mixed in a weight ratio of 4:1.

FORMULATION EXAMPLE 5

Wettable powder

| | | |
|---|---|---|
| (a) Compound No. 16-b | 10 | parts by weight |
| (b) Diatomaceous earth | 69 | parts by weight |
| (c) Calcium carbonate powder | 15 | parts by weight |
| (d) Dialkylsulfosuccinate | 1 | parts by weight |
| (e) Polyoxyethylene alkylaryl sulfate | 3 | parts by weight |
| (f) Sodium β-naphthalene-sulfonate-formaldehyde condensate | 2 | parts by weight |

The above components are uniformly mixed.

FORMULATION EXAMPLE 6

Wettable powder

| | | |
|---|---|---|
| (a) Compound No. 17-b | 20 | parts by weight |
| (b) Kaolin | 62.4 | parts by weight |
| (c) Fine silica | 12.8 | parts by weight |
| (d) Alkylaryl sulfonate | 1.6 | parts by weight |
| (e) Polyoxyethylene alkylaryl sulfate | 2.4 | parts by weight |
| (f) Polyoxyethylene alkylaryl ether | 0.8 | parts by weight |

The above components are uniformly mixed.

FORMULATION EXAMPLE 7

Dust

| | | |
|---|---|---|
| (a) Compound No. 23 | 5 | parts by weight |
| (b) Talc | 94.5 | parts by weight |
| (c) Lower alcohol phosphate | 0.5 | parts by weight |

The above components are uniformly mixed.

FORMULATION EXAMPLE 8

Dust

| | | |
|---|---|---|
| (a) Compound No. 16-b | 0.2 | parts by weight |
| (b) Calcium carbonate powder | 98.8 | parts by weight |
| (c) Lower alcohol phosphate | 1.0 | parts by weight |

The above components are uniformly mixed.

FORMULATION EXAMPLE 9

Emulsifiable concentrate

| | | |
|---|---|---|
| (a) Compound No. 26 | 20 | parts by weight |
| (b) Xylene | 60 | parts by weight |
| (c) Polyoxyethylene alkylaryl ether | 20 | parts by weight |

The above components are mixed and dissolved.

FORMULATON EXAMPLE 10

Suspension concentrate

| | | |
|---|---|---|
| (a) Compound No. 151 | 10 | parts by weight |
| (b) Corn oil | 77 | parts by weight |
| (c) Polyoxyethylene caster oil | 12 | parts by weight |
| (d) Bentonite-alkylamine complex | 1 | parts by weight |

The above components are uniformly mixed and pulverized.

FORMULATION EXAMPLE 11

Granule

| | | |
|---|---|---|
| (a) Compound No. 33-b | 1 | parts by weight |
| (b) Bentonite | 61 | parts by weight |
| (c) Kaolin | 33 | parts by weight |
| (d) Sodium lignin sulfonate | 5 | parts by weight |

A suitable amount of water required is added to the above components, followed by mixing and granulating.

While the invention has been described in detail and with reference to specific embodiments thereof, it will be apparent to one skilled in the art that various changes and modifications can be made therein without departing from the spirit and scope thereof.

What is claimed is:

1. An imidazole compound represented by the following general formula (I):

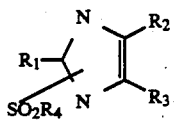

wherein:
$R_1$ represents a cyano group or a $-CSNHR_5$ group, wherein $R_5$ represents a hydrogen atom, a $C_{1-4}$ alkyl group, or a $-COR_6$ group, wherein $R_6$ represents a $C_{1-4}$ alkyl group, a halogenated $C_{1-4}$ alkyl group, or a phenyl group;
$R_2$ and $R_3$ represents a hydrogen atom; a halogen atom; a nitro group; a cyano group; a trimethylsilyl group; a $C_{3-6}$ cycloalkyl group; a naphthyl group; a $C_{1-12}$ alkyl group which is optionally substituted with one or more halogen atoms, hydroxyl groups, acetoxy groups, $C_{1-4}$ alkoxy groups, halogenated $C_{1-4}$ alkoxy groups, phenyl groups, halogenated phenyl groups, or $C_{1-4}$ alkylated phenyl groups; a $C_{2-10}$ alkenyl group which is optionally substituted with one or more halogen atoms; a $C_{1-6}$ alkoxy group which is optionally substituted with one or more halogen atoms; a phenyl group which is optionally substituted with one or more halogen atoms, $C_{1-4}$ alkyl groups, halogenated $C_{1-4}$ alkyl groups, $C_{1-4}$ alkoxy groups, halogenated $C_{1-4}$ alkoxy groups, $C_{1-4}$ alkylthio groups, halogenated $C_{1-4}$ alkylthio groups, nitro groups, cyano groups, or 3,4-methylenedioxy groups; a furyl group which is optionally substituted with one or more halogen atoms or $C_{1-4}$ alkyl groups; a thienyl group which is optionally substituted with one or more halogen atoms or $C_{1-4}$ alkyl groups; a pyridyl group which is optionally substituted with one or more halogen atoms or $C_{1-4}$ alkyl groups; an $-SO_nR_7$ group, wherein $R_7$ represents a $C_{1-6}$ alkyl group, a $C_{2-6}$ alkenyl group, a phenyl group which is optionally substituted with one or more halogen atoms, a benzyl group, a pyridyl group which is optionally substituted with one or more halogen atoms, $C_{1-4}$ alkyl groups, or halogenated $C_{1-4}$ alkyl groups; or an $-NR_8R_9$ group, wherein $R_8$ and $R_9$ each represents a $C_{1-4}$ alkyl group, and n is 0, 1, or 2; or a $-CO(NH)_mR_{10}$ group, wherein $R_{10}$ represents a $C_{1-4}$ alkyl group which is optionally substituted with one or more halogen atoms, a $C_{1-4}$ alkoxy group which is optionally substituted with one or more halogen atoms, or a phenyl group which is optionally substituted with one or more halogen atoms; and m is 0 or 1; and
$R_4$ represents a $C_{1-6}$ alkyl group which is optionally substituted with one or more halogen atoms; a $C_{3-6}$ cycloalkyl group; a phenyl group; a thienyl group; or an $-NR_{11}R_{12}$ group, wherein $R_{11}$ and $R_{12}$ each represents a hydrogen atom, a $C_{1-4}$ alkyl group which is optionally substituted with one or more halogen atoms, a $C_{2-4}$ alkenyl group, of $R_{11}$ and $R_{12}$ are combined with each other together with a nitrogen atom adjacent thereto to form a pyrrolidinyl group, a piperidinyl group, a morpholino group, or a thiomorpholino group, provided that $R_{11}$ and $R_{12}$ are not simultaneously a hydrogen atom;

provided that $R_2$ and $R_3$ are not simultaneously a halogen atom.

2. The compound according to claim 1, wherein $R_1$ represents a cyano group.

3. The compound according to claim 1, wherein $R_1$ represents a cyano group; $R_2$ and $R_3$ each represents a hydrogen atom; a halogen atom; a nitro group; a cyano group; a $C_{1-12}$ alkyl group which is optionally substituted with one or more halogen atoms, hydroxyl groups, $C_{1-4}$ alkoxy groups, phenyl groups, halogenated phenyl groups, or $C_{1-4}$ alkylated phenyl groups; a $C_{2-10}$ alkenyl group which is optionally substituted with one or more halogen atoms; a phenyl group which is optionally substituted with one or more halogen atoms, $C_{1-4}$ alkyl groups, $C_{1-4}$ alkoxy groups, halogenated $C_{1-4}$ alkoxy groups, or nitro groups; an $-SO_nR_7$ group, wherein $R_7$ represents a $C_{1-6}$ alkyl group, a phenyl group which is optionally substituted with one or more halogen atoms, or an $-NR_8R_9$ group, wherein $R_8$ and $R_9$ each represents a $C_{1-4}$ alkyl group, and n is 0, 1 or 2; or a $-CONHR_{10}$ group, wherein $R_{10}$ represents a phenyl group which is optionally substituted with one or more halogen atoms; and $R_4$ represents a $C_{1-6}$ alkyl group or an $-NR_{11}R_{12}$ group, wherein $R_{11}$ and $R_{12}$ each represents a $C_{1-4}$ alkyl group; provided that $R_2$ and $R_3$ are not simultaneously a halogen atom.

4. The compound according to claim 1, wherein $R_1$ represents a cyano group; $R_2$ represents a hydrogen atom; a $C_{1-12}$ alkyl group which is optionally substituted with one or more halogen atoms, phenyl groups, or halogenated phenyl groups; a $C_{2-4}$ alkenyl group; a phenyl group which is optionally substituted with one or more halogen atoms, $C_{1-4}$ alkyl groups, $C_{1-4}$ alkoxy groups, or halogenated $C_{1-4}$ alkoxy groups; a $C_{1-6}$ alkylthio group; or a phenylthio group which is optionally substituted with one or more halogen atoms; $R_3$ represents a hydrogen atom; a halogen atom; or a cyano group; and $R_4$ represents an $-N(CH_3)_2$ group.

5. The compound according to claim 1, wherein $R_4$ represents $-N(CH_3)_2$ group.

6. The compound according to claim 1, wherein $R_1$ represents a cyano group, and $R_4$ represents an $-N(CH_3)_2$ group.

7. The compound according to claim 1, wherein $R_1$ represents a cyano group; $R_2$ represents a $C_{1-12}$ alkyl group which is optionally substituted with one or more halogen atoms, phenyl groups, or halogenated phenyl groups; a $C_{2-4}$ alkenyl group; a phenyl group which is optionally substituted with one or more halogen atoms; or a $C_{1-6}$ alkylthio group; $R_3$ represents a halogen atom; and $R_4$ represents an $-N(CH_3)_2$ group.

8. The compound according to claim 1, wherein $R_1$ represents a cyano group; $R_2$ represents a $C_{1-12}$ alkyl group or a phenyl group; $R_3$ represents a chlorine atom; and $R_4$ represents an $-N(CH_3)_2$ group.

9. A biocidal composition which comprises an imidazole compound, as an active ingredient, represented by the following general formula (I):

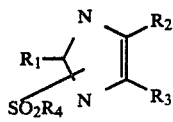

(I)

wherein:
R$_1$ represents a cyano group or a —CSNHR$_5$ group, wherein R$_5$ represents a hydrogen atom, a C$_{1-4}$ alkyl group, or a —COR$_6$ group, wherein R$_6$ represents a C$_{1-4}$ alkyl group, a halogenated C$_{1-4}$ alkyl group, or a phenyl group;

R$_2$ and R$_3$ each represents a hydrogen atom; a halogen atom; a nitro group; a cyano group; a trimethylsilyl group; a C$_{3-6}$ cycloalkyl group; a naphthyl group; a C$_{1-12}$ alkyl group which is optionally substituted with one or more halogen atoms, hydroxyl groups, acetoxy groups, C$_{1-4}$ alkoxy groups, halogenated C$_{1-4}$ alkoxy groups, phenyl groups, halogenated phenyl groups, or C$_{1-4}$ alkylated phenyl groups; a C$_{2-10}$ alkenyl group which is optionally substituted with one or more halogen atoms; a C$_{1-6}$ alkoxy group which is optionally substituted with one or more halogen atoms; a phenyl group which is optionally substituted with one or more halogen atoms, C$_{1-4}$ alkyl groups, halogenated C$_{1-4}$ alkyl groups, C$_{1-4}$ alkoxy groups, halogenated C$_{1-4}$ alkoxy groups, C$_{1-4}$ alkylthio groups, halogenated C$_{1-4}$ alkylthio groups, nitro groups, cyano groups, or 3,4-methylenedioxy groups; a furyl group which is optionally substituted with one or more halogen atoms or C$_{1-4}$ alkyl groups; a thienyl group which is optionally substituted with one or more halogen atoms or C$_{1-4}$ alkyl groups; a pyridyl group which is optionally substituted with one or more halogen atoms or C$_{1-4}$ alkyl groups; an —SO$_n$R$_7$ group, wherein R$_7$ represents a C$_{1-6}$ alkyl group, a C$_{2-6}$ alkenyl group, a phenyl group which is optionally substituted with one or more halogen atoms, a benzyl group, a pyridyl group which is optionally substituted with one or more halogen atoms, C$_{1-4}$ alkyl groups, or halogenated C$_{1-4}$ alkyl groups; or an —NR$_8$R$_9$ group, wherein R$_8$ and R$_9$ each represents a C$_{1-4}$ alkyl group, and n is 0, 1, or 2; or a —CO(NH)$_m$R$_{10}$ group, wherein R$_{10}$ represents a C$_{1-4}$ alkyl group which is optionally substituted with one or more halogen atoms, a C$_{1-4}$ alkoxy group which is optionally substituted with one or more halogen atoms, or a phenyl group which is optionally substituted with one or more halogen atoms; and m is 0 or 1; and R$_4$ represents a C$_{1-6}$ alkyl group which is optionally substituted with one or more halogen atoms; a C$_{3-6}$ cycloalkyl group; a phenyl group; a thienyl group; or an —NR$_{11}$R$_{12}$ group, wherein R$_{11}$ and R$_{12}$ each represents a hydrogen atom, a C$_{1-4}$ alkyl group which is optionally substituted with one or more halogen atoms, a C$_{2-4}$ alkenyl group, or R$_{11}$ and R$_{12}$ are combined with each other together with a nitrogen atom adjacent thereto to form a pyrrolidinyl group, a piperidinyl group, a morpholino group, or a thiomorphol group, provided that R$_{11}$ and R$_{12}$ are not simultaneously a hydrogen atom;

provided that R$_2$ and R$_3$ are not simultaneously a halogen atom; and adjuvants.

* * * * *

UNITED STATES PATENT AND TRADEMARK OFFICE
CERTIFICATE OF CORRECTION

PATENT NO. : 4,995,898

DATED : Feb. 26, 1991

INVENTOR(S) : Rikuo Nasu, et al.

It is certified that error appears in the above-identified patent and that said Letters Patent is hereby corrected as shown below:

On the Title page, item [57]
In the ABSTRACT, third line thereof, delete the formula

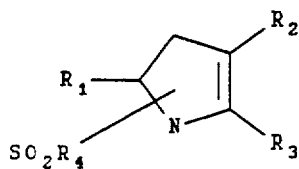

and insert

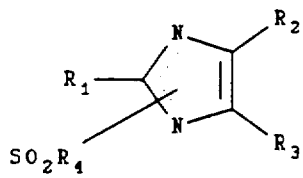

UNITED STATES PATENT AND TRADEMARK OFFICE
CERTIFICATE OF CORRECTION

PATENT NO. : 4,995,898
DATED : Feb. 26, 1991
INVENTOR(S) : Rikuo Nasu, et al.

It is certified that error appears in the above-identified patent and that said Letters Patent is hereby corrected as shown below:

Column 3, line 48, delete the formula

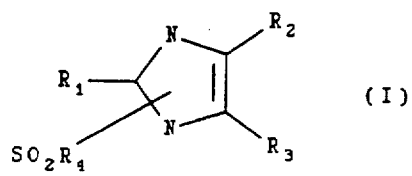

and insert

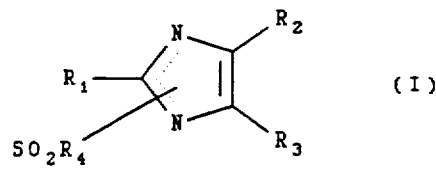

UNITED STATES PATENT AND TRADEMARK OFFICE
CERTIFICATE OF CORRECTION

PATENT NO. : 4,995,898

DATED : Feb. 26, 1991

INVENTOR(S) : Rikuo Nasu, et al.

It is certified that error appears in the above-identified patent and that said Letters Patent is hereby corrected as shown below:

Column 6, lines 55-60, delete the formula

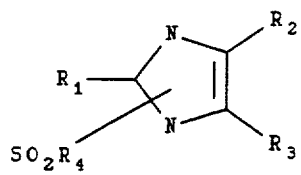

(I)

and insert

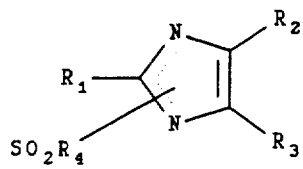

(I)

UNITED STATES PATENT AND TRADEMARK OFFICE
CERTIFICATE OF CORRECTION

PATENT NO. : 4,995,898
DATED : Feb. 26, 1991
INVENTOR(S) : Rikuo Nasu, et al.

It is certified that error appears in the above-identified patent and that said Letters Patent is hereby corrected as shown below:

Column 7, lines 10-15, delete the formula

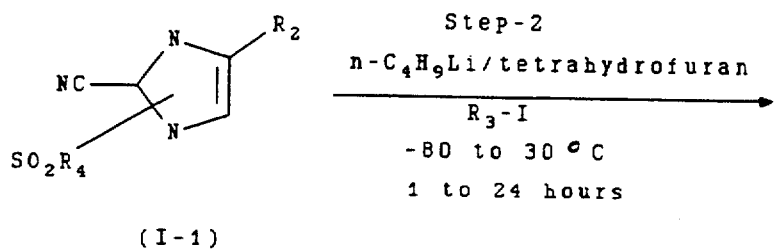

and insert

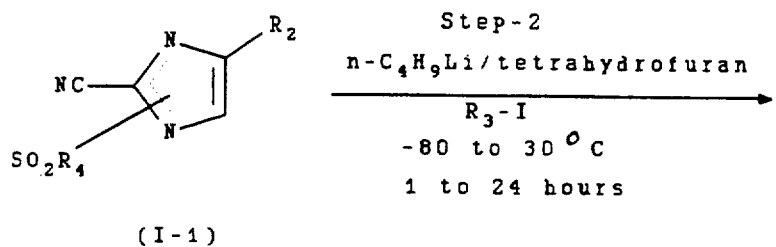

UNITED STATES PATENT AND TRADEMARK OFFICE
CERTIFICATE OF CORRECTION

PATENT NO. : 4,995,898

DATED : Feb. 26, 1991

INVENTOR(S) : Rikuo Nasu, et al.

It is certified that error appears in the above-identified patent and that said Letters Patent is hereby corrected as shown below:

Column 8, lines 15-35, delete formulae (I-5), (I-6) and (I-7) and insert corrected formula (I-5), (I-6) and (I-7)

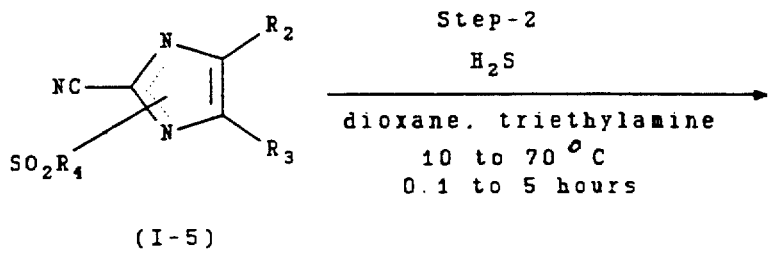

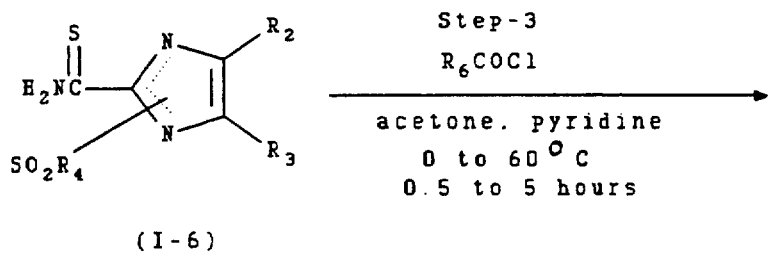

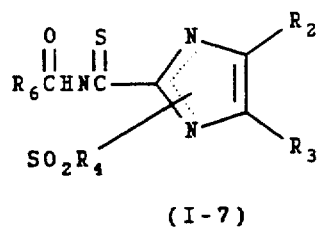

UNITED STATES PATENT AND TRADEMARK OFFICE
CERTIFICATE OF CORRECTION

PATENT NO. : 4,995,898

DATED : Feb. 26, 1991

INVENTOR(S) : Rikuo Nasu, et al.

It is certified that error appears in the above-identified patent and that said Letters Patent is hereby corrected as shown below:

Delete columns 9, 10, 11, 12, 13 and 14, and insert therefor the following columns 9, 10, 11, 12, 13 and 14.

a chlorine atom, a bromine atom, an iodine atom, and a fluorine atom; of these, preferred is a chlorine atom.
In the reaction scheme described above, the compounds represented by the general formula (III) are known compounds, and the compounds represented by the general formula (II) can be prepared by either one of the following processes.
(1)
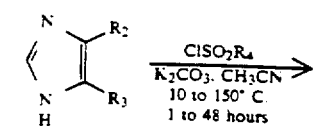
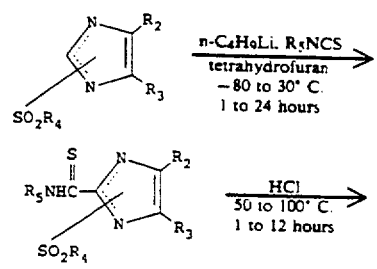
(2)
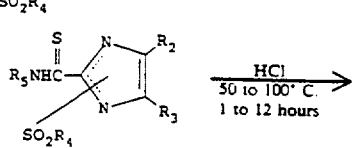
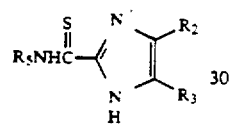
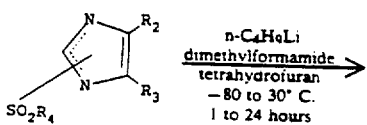
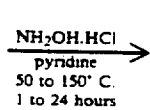
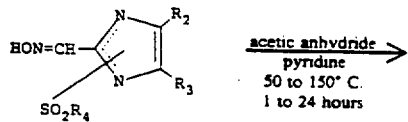
(3)
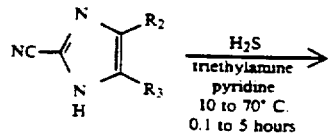
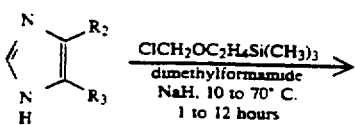
-continued
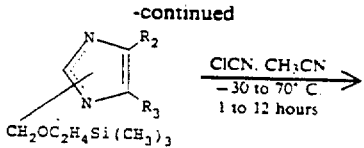
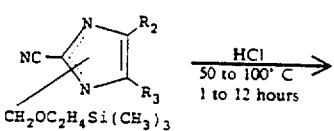
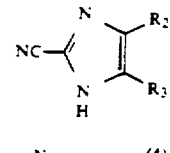
(4)
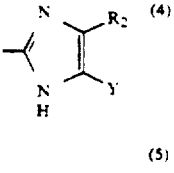
(5)
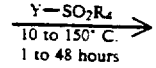
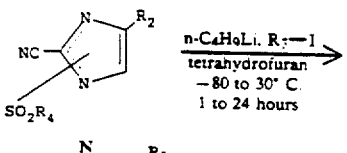
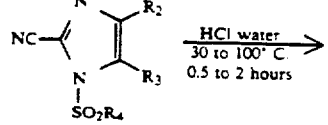
(6)
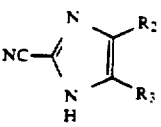
(7)
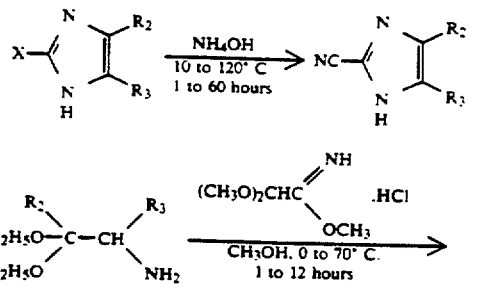
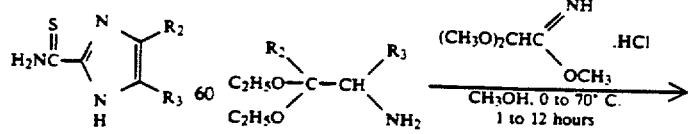
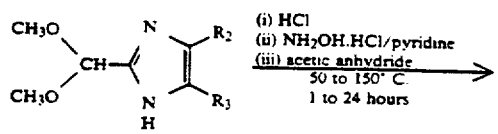

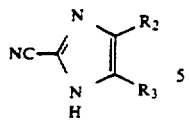
-continued
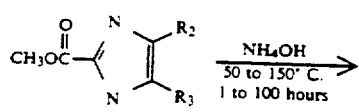
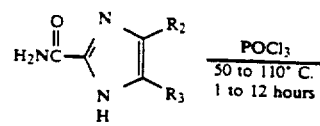
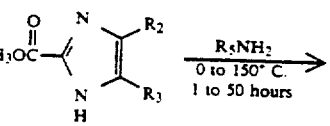
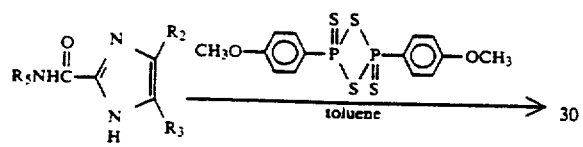
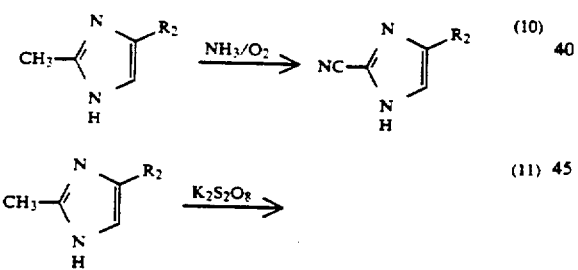
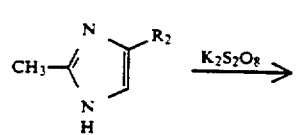
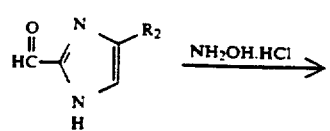
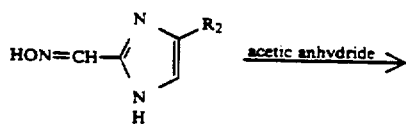
-continued
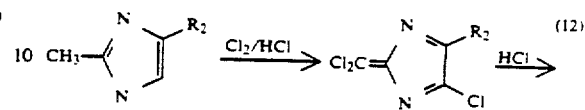
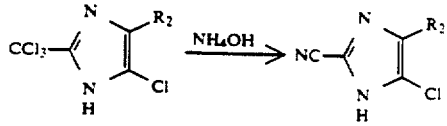
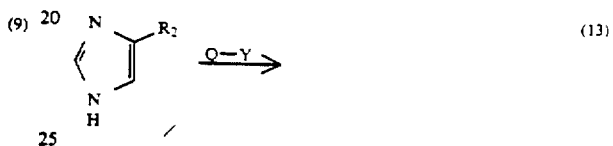
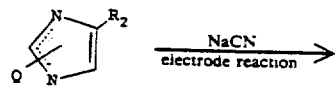
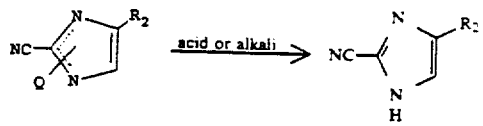
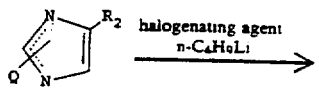
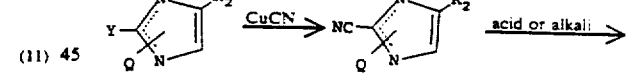
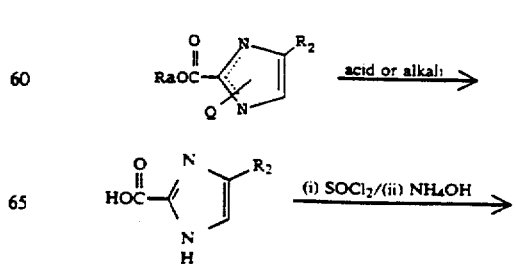

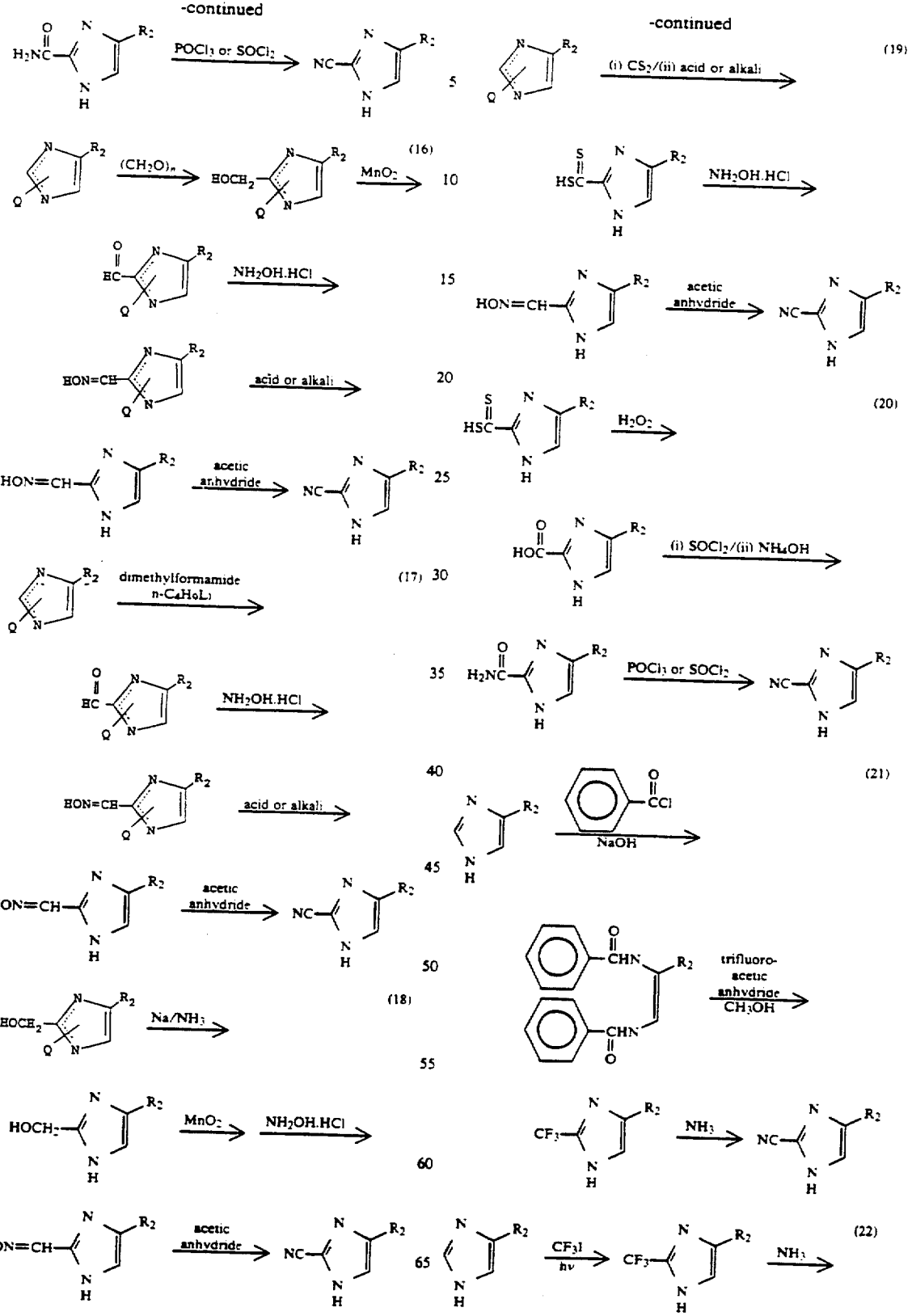

UNITED STATES PATENT AND TRADEMARK OFFICE
CERTIFICATE OF CORRECTION

PATENT NO. : 4,995,898

DATED : Feb. 26, 1991

INVENTOR(S) : Rikuo Nasu, et al.

It is certified that error appears in the above-identified patent and that said Letters Patent is hereby corrected as shown below:

Columns 31 and 32, delete formula at top of Table 2 and insert

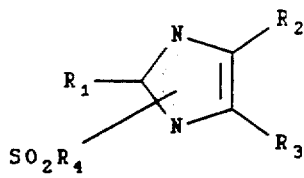

Columns 33 and 34, delete the formula at the top of Table 2-continued and insert

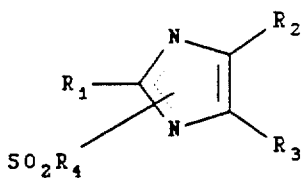

Columns 35 and 36, delete the formula at the top of Table 2-continued and insert

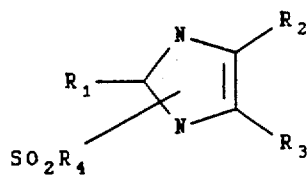

UNITED STATES PATENT AND TRADEMARK OFFICE
CERTIFICATE OF CORRECTION

PATENT NO. : 4,995,898

DATED : Feb. 26, 1991

INVENTOR(S) : Rikuo Nasu, et al.

It is certified that error appears in the above-identified patent and that said Letters Patent is hereby corrected as shown below:

Columns 37 and 38, delete the formula at the top of Table 2-continued and insert

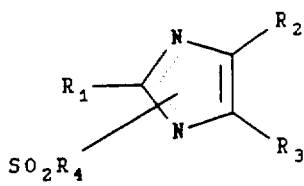

Columns 39 and 40, delete the formula at the top of Table 2-continued and insert

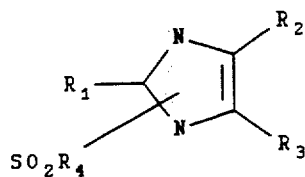

Columns 41 and 42, delete the formula at the top of Table 2-continued and insert

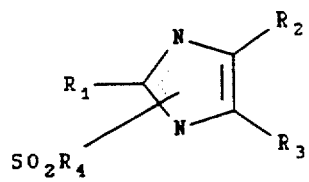

UNITED STATES PATENT AND TRADEMARK OFFICE
CERTIFICATE OF CORRECTION

PATENT NO. : 4,995,898

DATED : Feb. 26, 1991

INVENTOR(S) : Rikuo Nasu, et al.

It is certified that error appears in the above-identified patent and that said Letters Patent is hereby corrected as shown below:

Columns 43 and 44, delete the formula at the top of Table 2-continued and insert

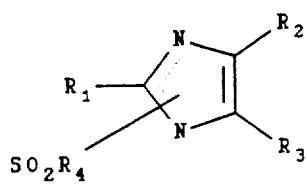

Column 61, lines 8-14, delete the formula

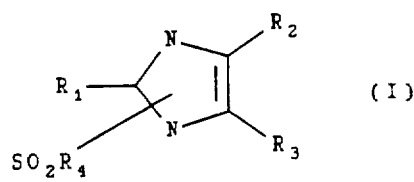

(I)

and insert

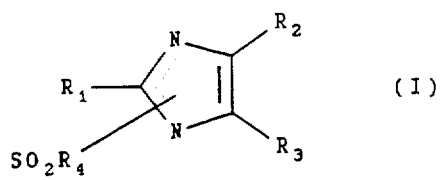

(I)

UNITED STATES PATENT AND TRADEMARK OFFICE
CERTIFICATE OF CORRECTION

PATENT NO. : 4,995,898
DATED : Feb. 26, 1991
INVENTOR(S) : Riku Nasu, et al.

It is certified that error appears in the above-identified patent and that said Letters Patent is hereby corrected as shown below:

Column 63, lines 1-8, delete the formula

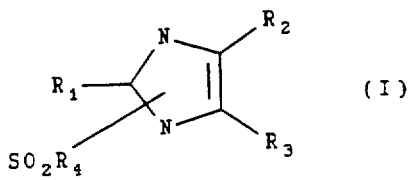

and insert

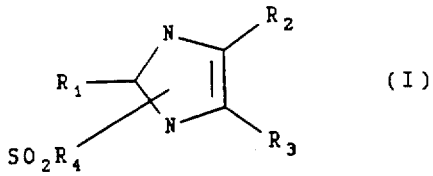

Signed and Sealed this

Thirtieth Day of November, 1993

Attest:

BRUCE LEHMAN

Attesting Officer  Commissioner of Patents and Trademarks